(12) United States Patent
Hagadorn et al.

(10) Patent No.: US 9,290,519 B2
(45) Date of Patent: Mar. 22, 2016

(54) PYRIDYLDIAMIDO TRANSITION METAL COMPLEXES, PRODUCTION AND USE THEREOF

(71) Applicant: ExxonMobil Chemical Patents Inc., Baytown, TX (US)

(72) Inventors: John R. Hagadorn, Houston, TX (US); Ilya S. Borisov, Moscow (RU); Arkady K. Golenishchev, Moscow (RU); Georgy P. Goryunov, Moscow (RU); Dmitry V. Uborsky, Moscow (RU); Alexander Z. Voskoboynikov, Moscow (RU)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/511,752

(22) Filed: Oct. 10, 2014

(65) Prior Publication Data

US 2015/0141601 A1    May 21, 2015

Related U.S. Application Data

(60) Provisional application No. 61/904,551, filed on Nov. 15, 2013.

(51) Int. Cl.
| | |
|---|---|
| C08F 4/76 | (2006.01) |
| C07F 7/00 | (2006.01) |
| C07F 7/02 | (2006.01) |
| C08F 4/659 | (2006.01) |

(52) U.S. Cl.
CPC . *C07F 7/00* (2013.01); *C07F 7/025* (2013.01); *C08F 4/659* (2013.01)

(58) Field of Classification Search
CPC .................................................. C08F 4/64148
USPC ......................................... 526/172, 161, 134
See application file for complete search history.

(56) References Cited

U.S. PATENT DOCUMENTS

| | | | |
|---|---|---|---|
| 6,103,657 | A  | 8/2000  | Murray |
| 6,175,409 | B1 | 1/2001  | Nielsen et al. |
| 6,260,407 | B1 | 7/2001  | Petro et al. |
| 6,294,388 | B1 | 9/2001  | Petro |
| 6,306,658 | B1 | 10/2001 | Turner et al. |
| 6,406,632 | B1 | 6/2002  | Safir et al. |
| 6,436,292 | B1 | 8/2002  | Petro |
| 6,454,947 | B1 | 9/2002  | Safir et al. |
| 6,455,316 | B1 | 9/2002  | Turner et al. |
| 6,461,515 | B1 | 10/2002 | Safir et al. |
| 6,475,391 | B2 | 11/2002 | Safir et al. |
| 6,489,168 | B1 | 12/2002 | Wang et al. |
| 6,491,823 | B1 | 12/2002 | Safir et al. |

(Continued)

FOREIGN PATENT DOCUMENTS

| | | |
|---|---|---|
| WO | WO 00/09255 | 2/2000 |
| WO | WO 02/38638 | 5/2002 |

(Continued)

OTHER PUBLICATIONS

U.S. Appl. No. 14/511,752, filed Oct. 10, 2014, Hagadorn et al.

(Continued)

*Primary Examiner* — Rip A Lee

(57) ABSTRACT

Pyridyldiamido transition metal complexes are disclosed for use in alkene polymerization.

27 Claims, 3 Drawing Sheets

(56) References Cited

U.S. PATENT DOCUMENTS

| | | | |
|---|---|---|---|
| 6,900,321 | B2 | 5/2005 | Boussie et al. |
| 7,164,020 | B2 | 1/2007 | Vogel et al. |
| 7,858,817 | B2 | 12/2010 | Hagadorn |
| 7,910,760 | B2 | 3/2011 | Hagadorn |
| 7,973,116 | B2 | 7/2011 | Hagadorn et al. |
| 8,163,853 | B2 | 4/2012 | Hagadorn |
| 8,212,047 | B2 | 7/2012 | Hagadorn et al. |
| 8,394,902 | B2 | 3/2013 | Hagadorn et al. |
| 8,557,933 | B2 | 10/2013 | Hagadorn et al. |
| 2002/0142912 | A1 | 10/2002 | Boussie et al. |
| 2004/0220050 | A1 | 11/2004 | Frazier et al. |
| 2010/0022726 | A1 | 1/2010 | Hagadorn et al. |
| 2010/0227990 | A1* | 9/2010 | Kuhlman et al. ............ 526/170 |
| 2011/0224391 | A1 | 9/2011 | Hagadorn et al. |
| 2011/0301310 | A1 | 12/2011 | Hagadorn et al. |
| 2012/0016092 | A1 | 1/2012 | Nagy et al. |
| 2012/0071616 | A1 | 3/2012 | Hagadorn et al. |
| 2013/0131294 | A1 | 5/2013 | Hagadorn et al. |
| 2014/0221587 | A1 | 8/2014 | Hagadorn et al. |
| 2014/0256893 | A1 | 9/2014 | Hagadorn et al. |

FOREIGN PATENT DOCUMENTS

| | | |
|---|---|---|
| WO | WO 2005/095469 | 10/2005 |
| WO | WO 2006/036748 | 4/2006 |
| WO | WO 2007/067965 | 6/2007 |
| WO | WO 2010/011435 | 1/2010 |
| WO | WO 2010/037059 | 4/2010 |
| WO | WO 2012/134614 | 10/2012 |

OTHER PUBLICATIONS

U.S. Appl. No. 14/540,118, filed Nov. 13, 2014, Hagadorn et al.
U.S. Appl. No. 61/815,065, filed Apr. 23, 2013, Hagadorn et al.
U.S. Appl. No. 61/904,551, filed Nov. 15, 2013, Hagadorn et al.
U.S. Appl. No. 61/947,052, filed Mar. 3, 2014, Hagadorn et al.
U.S. Appl. No. 62/011,947, filed Jun. 13, 2014, Hagadorn et al.
U.S. Appl. No. 62/137,417, filed Mar. 24, 2015, Atienza et al.
U.S. Appl. No. 62/149,807, filed Apr. 20, 2015, Ye et al.
U.S. Appl. No. 62/149,818, filed Apr. 20, 2015, Ye et al.
U.S. Appl. No. 62/153,749, filed Apr. 28, 2015, Walzer et al.
Boussie et al., "*A Fully Integrated High-Throughput Screening Methodology for the Discovery of New Polyolefin Catalysts: Discovery of a New Class of High Temperature Single-Site Group (IV) Copolymerization Catalysts*," J. Am. Chem. Soc. 2003, vol. 125, pp. 4306-4317.
Britovsek et al., "*The Search for New-Generation Olefin Polymerization Catalysts: Life beyond Metallocenes*," Angew. Chem. Int. Ed. 1999, vol. 38, pp. 428-447.
Froese et al., "*Mechanism of Activation of a Hafnium Pyridyl-Amide Olefin Polymerization Catalyst: Ligand Modification by Monomer*," J. Am. Chem. Soc. 2007, vol. 129, pp. 7831-7840.
Gibson et al., "*Advances in Non-Metallocene Olefin Polymerization Catalysts*," Chem. Rev. 2003, vol. 103, pp. 283-315.
Guerin et al., "*Conformationally Rigid Diamide Complexes of Zirconium: Electron Deficient Analogues of $Cp_2Zr$*," Organometallics 1996, vol. 15, p. 5586-5590.
McGuire Jr. et al., "*Platinum(II) polypyridines: A tale of two axes*," Coordination Chemistry Reviews, Elsevier Science, Amsterdam, NL, vol. 254, No. 21-22, Nov. 1, 2010, pp. 2574-2583.
Vaughan et al., "*3.20 Industrial catalysts for alkene polymerization*," Polymer Science: A Comprehensive Reference, vol. 3, Chapter 20, pp. 657-672.

\* cited by examiner

PYRIDYLDIAMIDO TRANSITION METAL COMPLEXES, PRODUCTION AND USE THEREOF

PRIORITY

This application claims priority to and the benefit of U.S. Ser. No. 61/904,551, filed Nov. 15, 2013.

FIELD OF INVENTION

The invention relates to pyridyldiamido transition metal complexes and intermediates and processes for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components for use in the polymerization of alkenes, see for example US 2002/0142912; U.S. Pat. No. 6,900,321; and U.S. Pat. No. 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, pp. 7831-7840) to form an active catalyst that has both five-membered and a seven-membered chelate rings.

WO 2010/037059 discloses pyridine containing amines for use in pharmaceutical applications.

US 2010/0227990 A1 discloses ligands that bind to the metal center with a NNC donor set instead of an NNN or NNP donor set.

WO/0238628 A2 discloses ligands that bind to the metal center with a NNC donor set instead of an NNN or NNP donor set.

Guerin, F.; McConville, D. H.; Vittal, J. J. Organometallics 1996, 15, p. 5586 discloses a ligand family and group 4 complexes that use a NNN-donor set, but do not feature 7-membered chelate ring or either of dihydroindenyl- and tetrahydronaphthalenyl-groups.

U.S. Pat. No. 7,973,116, U.S. Pat. No. 8,394,902, US 2011-0224391, US 2011-0301310 A1, and U.S. Ser. No. 61/815,065, filed Apr. 23, 2013 disclose pyridylamido transition metal complexes that do not feature dihydroindenyl- or tetrahydronaphthalenyl-groups.

References of interest also include: 1) Vaughan, A; Davis, D. S.; Hagadorn, J. R. in Comprehensive Polymer Science, Vol. 3, Chapter 20, "Industrial catalysts for alkene polymerization"; 2) Gibson, V. C.; Spitzmesser, S. K. Chem. Rev. 2003, 103, 283; 3) Britovsek, G. J. P.; Gibson, V. C.; Wass, D. F. Angew. Chem. Int. Ed. 1999, 38, 428; 4) WO 06/036748; and 5) McGuire R. et al. Levason Bill et al, Platinum(II) polypyridines: A tale of two axes", Coordination Chemistry Reviews, Elsevier Science, Amsterdam, NL, vol. 254, no. 21-22, 1 Nov. 2010, pp. 2574, 2583, XP027279924, ISSN: 0010-8454.

There still is need for adding synthetic routes to widen the range of catalyst complexes that may be prepared and broaden their performance in alkene polymerization. The performance may be varied in respect of the amount of polymer produced per amount of catalyst (generally referred to as the "activity") under the prevailing polymerization conditions; the molecular weight and molecular weight distribution achieved at a given temperature; and/or the placement of higher alpha-olefins in terms of the degree of stereoregular placement. In particular, improvement of catalyst activity is of interest in the industry as it directly impacts economic feasibility.

SUMMARY OF INVENTION

This invention relates to novel transition metal complexes having tridentate ligands, such as tridentate NNN or NNP ligands. The ligand may be derived from a neutral ligand precursor or be created in situ in a complex. This invention also relates to pyridyldiamido transition metal complexes represented by the general formula (A), (B), (C) or (D) and to catalyst systems comprising an activator and a pyridyldiamido transition metal complex represented by the formula (A), (B), (C) or (D):

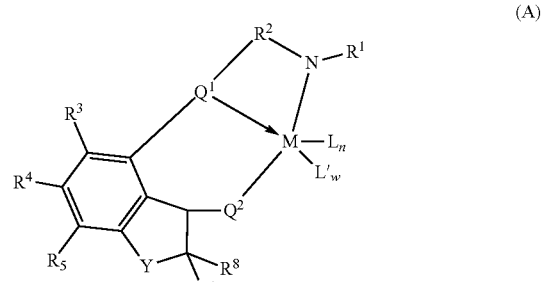

(A)

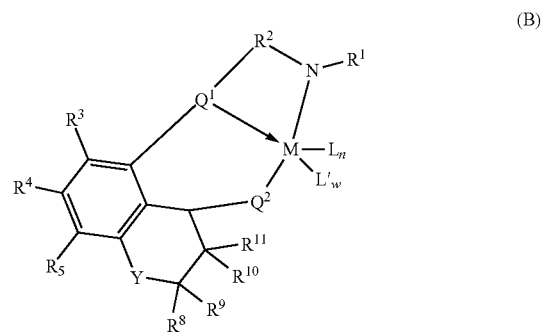

(B)

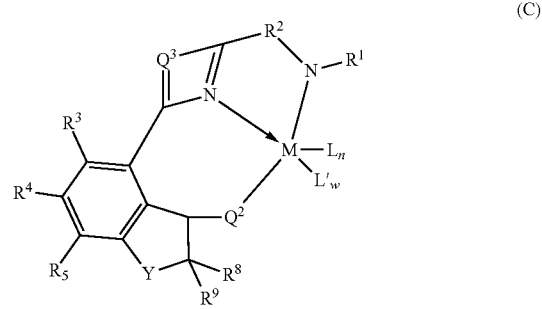

(C)

-continued

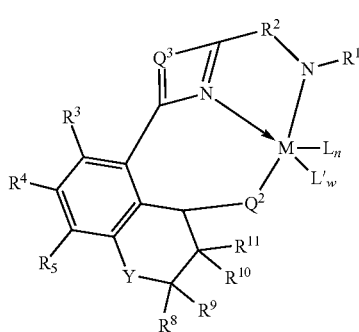

(D)

wherein:

M is a Group 3, 4, 5, 6, 7, 8, 9, 10, 11 or 12 metal;

$Q^1$ is a three atom bridge with the central of the three atoms being a group 15 or 16 element (said group 15 element may or may not be substituted with an $R^{30}$ group) that preferably forms a dative bond to M, preferably represented by the formula: -$G^1$-$G^2$-$G^3$- where $G^2$ is a group 15 or 16 atom (said group 15 element may be substituted with an $R^{30}$ group), $G^1$ and $G^3$ are each a group 14, 15 or 16 atom (each group 14, 15 and 16 element may or may not be substituted with one or more $R^{30}$ groups), where $G^1$, $G^2$ and $G^3$, or $G^1$ and $G^2$, or $G^1$ and $G^3$, or $G^2$ and $G^3$ may form a singular or multi ring system, where each $R^{30}$ group is, independently, hydrogen or a $C_1$ to $C_{100}$ hydrocarbyl group or a silyl group;

$Q^2$ is —$NR^{17}$, —$PR^{17}$, or oxygen, where $R^{17}$ is selected from hydrogen, hydrocarbyls, substituted hydrocarbyls, silyls, and germyls;

$Q^3$ is -(TT)- or -(TTT)- where each T is carbon or a heteroatom, preferably C, O, S, or N, and said carbon or heteroatom may be unsubstituted (e.g. hydrogen is bound to the carbon or heteroatom) or substituted with one or more $R^{30}$ groups that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$, and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^2$ is -E($R^{12}$)($R^{13}$)— with E being carbon, silicon, or germanium;

Y is selected from oxygen, sulfur, and -E*($R^6$)($R^7$)—, with E* being carbon, silicon, or germanium;

$R^6$, $R^7$, $R^8$, $R^9$, $R^{10}$, $R^{11}$, $R^{12}$, and $R^{13}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^8$ & $R^9$, and/or $R^9$ & $R^{10}$, and/or $R^{10}$ & $R^{11}$ and/or $R^{12}$ & $R^{13}$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4.

This invention further relates to a process to make the above complex, a process to make intermediates for the above complex and methods to polymerize olefins using the above complex.

DETAILED DESCRIPTION

Figure 1:
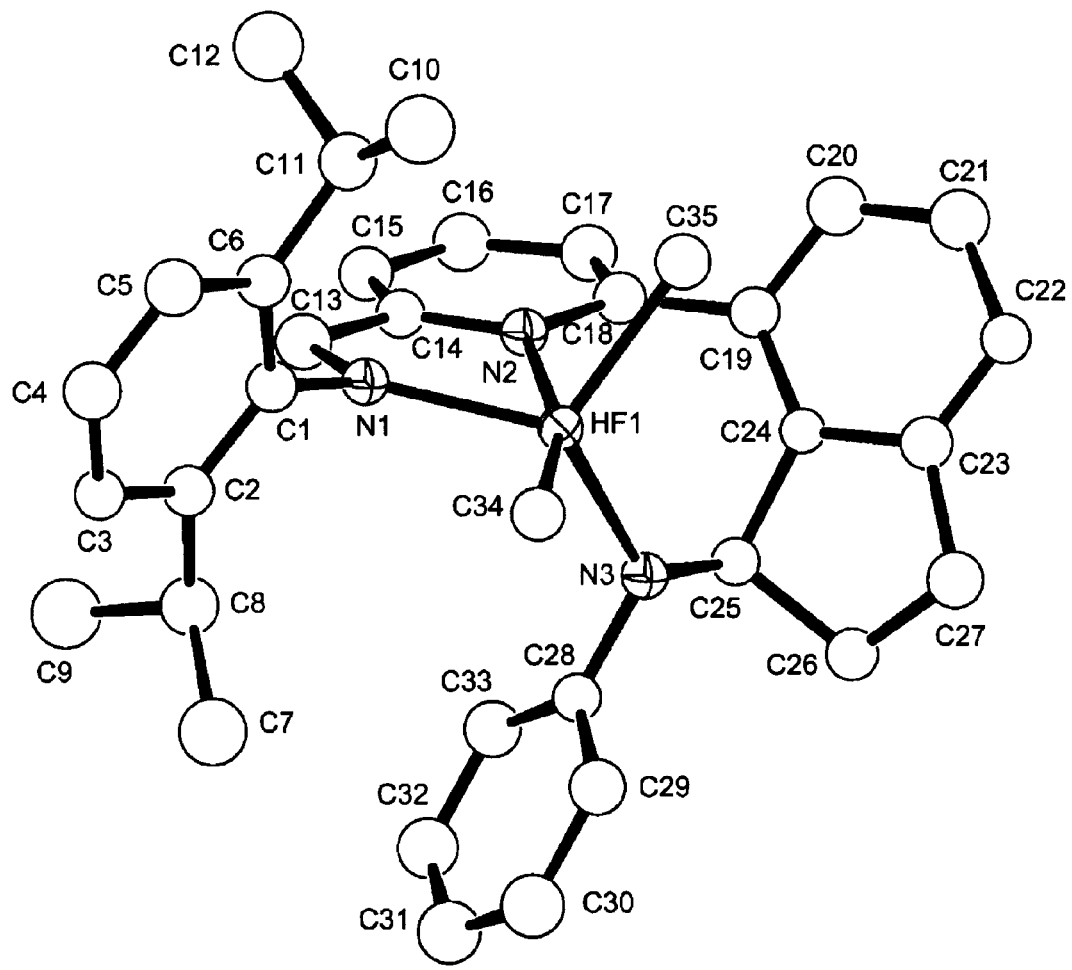
FIG. 1 is the molecular structure of complex 1 as determined by single-crystal X-ray diffraction.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

The following abbreviations are used through this specification: dme is 1,2-dimethoxyethane, Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is triisobutylaluminum, TNOAL is tri(n-octyl)aluminum, MAO is methylalumoxane, p-Me is para-methyl, Bn is benzyl (i.e., CH2Ph), THF (also referred to as thf) is tetrahydrofuran, RT is room temperature (and is 23° C. unless otherwise indicated), tol is toluene, EtOAc is ethyl acetate, and Cy is cyclohexyl.

The term "substituted" means that a hydrogen has been replaced with a heteroatom or a hydrocarbyl group. For example, methyl-cyclopentadiene is substituted with a methyl group.

The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be C1-C100 radicals, that may be linear, branched, or cyclic, and when cyclic, aromatic or non-aromatic.

Substituted hydrocarbyl radicals are radicals in which at least one hydrogen atom of the hydrocarbyl radical has been substituted with at least one functional group such as NR*2, OR*, SeR*, TeR*, PR*2, AsR*2, SbR*2, SR*, BR*2, SiR*3, GeR*3, SnR*3, PbR*3, and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer, can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

For purposes herein, an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and said derived units are present at 35 wt % to 55 wt %, based upon the weight of the copolymer.

For purposes herein a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such as an Mn of less than 25,000 g/mol, or in an embodiment less than 2,500 g/mol, or a low number of mer units, such as 75 mer units or less or 50 mer units or less. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

A higher α-olefin is defined to be an α-olefin having 4 or more carbon atoms.

Unless otherwise noted, all molecular weights units (e.g., Mw, Mn, Mz) are g/mol.

Unless otherwise noted all melting points (Tm) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or thee ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

In a first aspect of the invention, there is provided a pyridyldiamido transition metal complex (optionally, for use in alkene polymerization) represented by the general formula: (A), (B), (C), or (D) below and in another aspect there is provided a catalyst system comprising an activator and one or more pyridyldiamido transition metal complexes (optionally, for use in alkene polymerization) represented by the formula (A), (B), (C), or (D):

(A) 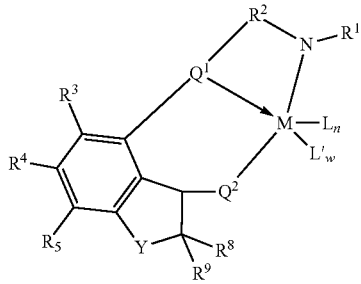

(B) 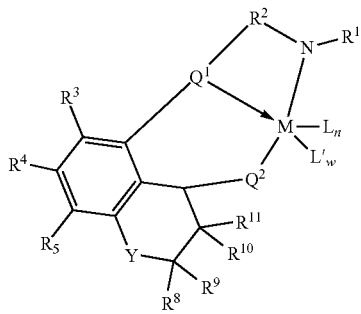

(C) 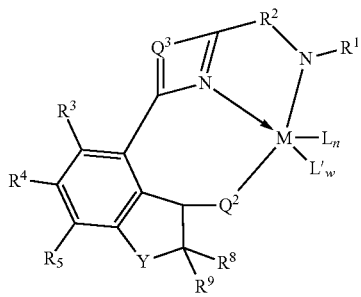

(D) 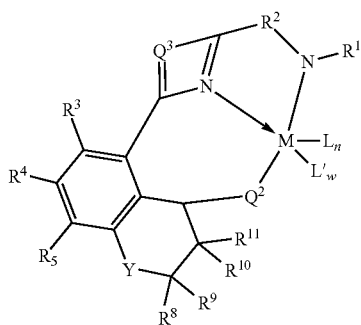

wherein:

M is a Group 3, 4, 5, 6, 7, 8, 9, 10, 11 or 12 metal (preferably a Group 4 metal, preferably Ti, Zr or Hf);

$Q^1$ is a three atom bridge with the central of the three atoms being a group 15 or 16 element (said group 15 element may or may not be substituted with an $R^{30}$ group) that preferably forms a dative bond to M, preferably represented by the formula: -$G^1$-$G^2$-$G^3$- where $G^2$ is a group 15 or 16 atom (said group 15 element may be substituted with a $R^{30}$ group), $G^1$ and $G^3$ are each a group 14, 15 or 16 atom (each group 14, 15 and 16 element may or may not be substituted with one or more $R^{30}$ groups), where $G^1$, $G^2$ and $G^3$, or $G^1$ and $G^2$, or $G^1$ and $G^3$, or $G^2$ and $G^3$ may form a singular or multi ring system, where each $R^{30}$ group is, independently, hydrogen or a $C_1$ to $C_{100}$ hydrocarbyl group or a silyl group;

$Q^2$ is —$NR^{17}$, —$PR^{17}$, or oxygen, where $R^{17}$ is selected from hydrogen, hydrocarbyls, substituted hydrocarbyls, silyl and germyl;

$Q^3$ is -(TT)- or -(TTT)- where each T is carbon or a heteroatom (preferably C, O, S, or N), and said carbon or heteroatom may or may not be substituted with one or more $R^{30}$ groups that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$, and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{10}$, $R^{11}$, $R^{12}$, and $R^{13}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^8$ & $R^9$, and/or $R^9$ & $R^{10}$, and/or $R^{10}$ & $R^{11}$ and/or $R^{12}$ & $R^{13}$) may be joined to form a saturated, substituted or unsubstituted hydrocarbyl or heterocyclic ring, where the ring has 5, 6, 7, or 8 ring carbon atoms and where substitutions on the ring can join to form additional rings;

$R^2$ is -E($R^{12}$)($R^{13}$)—, with E being carbon, silicon, or germanium (preferably carbon or silicon, preferably carbon) and $R^{12}$ and $R^{13}$ as described above;

Y is selected from oxygen, sulfur, and -E*($R^6$)($R^7$)—, with E* being carbon, silicon, or germanium (preferably carbon or silicon, preferably carbon) and $R^6$ and $R^7$ as described herein;

L is an anionic leaving group, where the L groups may be the same or different and any two L groups may be linked to form a dianionic leaving group;

n is 0, 1, 2, 3, or 4 (preferably 2);

L' is neutral Lewis base; and w is 0, 1, 2, 3 or 4 (preferably 0 or 1).

In a preferred embodiment of the invention, Q1 is one of the following:

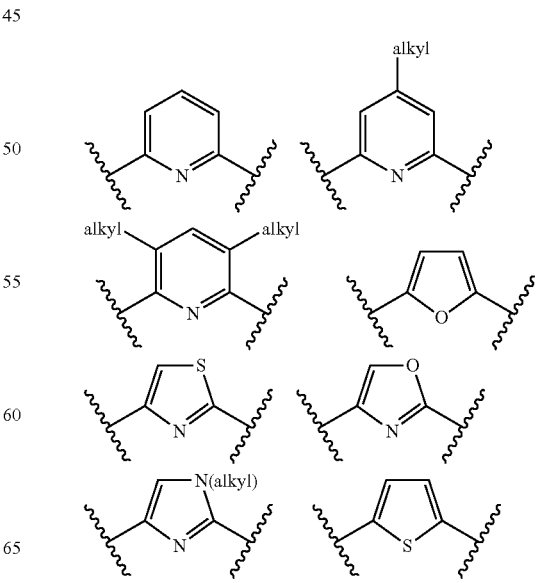

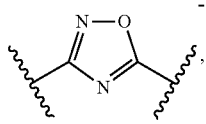

where the ⌇ symbols indicate the connections to $R^2$ and the aromatic ring, and alkyl is an alkyl group, such as a $C_1$ to $C_{20}$ alkyl group, such as methyl, ethyl, propyl, butyl, pentyl, hexyl, heptyl, octyl, nonyl, decyl, undecyl, or dodecyl.

In a preferred embodiment of the invention, G1 is carbon, nitrogen, oxygen, silicon, or sulfur, preferably carbon.

In a preferred embodiment of the invention, $G^2$ is nitrogen, phosphorous, oxygen, sulfur, or selenium, preferably nitrogen, oxygen, or sulfur.

In a preferred embodiment of the invention, $G^3$ is carbon, nitrogen, oxygen, silicon, or sulfur, preferably carbon.

In a preferred embodiment of the invention, Q2 is NR17, PR17, or oxygen, preferably NR17.

In a preferred embodiment of the invention, Q3 is CHCHCH, CHCH, CHN(alkyl), CH—S, CHC(alkyl)CH, C(alkyl)CHC(alkyl), CH—O, NO, preferably CHCHCH, CHCH, CHN(alkyl), CHN(Me), CH—S, preferably the alkyl is a C1 to C20 alkyl, such as methyl, ethyl, propyl, butyl, pentyl, hexyl, heptyl, octyl, nonyl, decyl, undecyl, or dodecyl.

In a preferred embodiment of the invention, R1 is selected from the group consisting of hydrocarbyls, substituted hydrocarbyls, and silyl groups (preferably alkyl, aryl, heteroaryl, and silyl groups, preferably methyl, ethyl, propyl, butyl, pentyl, hexyl, heptyl, octyl, nonyl, decyl, undecyl, dodecyl, phenyl, substituted phenyl, 2,6-disubstitutedphenyl, 2,6-diisopropylphenyl, 2,4-6-trisubstituted aryl, 2,4,6-triisopropylphenyl, and isomers thereof, including cyclohexyl).

In a preferred embodiment of the invention, $R^{17}$ is selected from the group consisting of hydrogen, hydrocarbyls, substituted hydrocarbyls, silyl, and germyl groups (preferably alkyl, aryl, heteroaryl, and silyl groups, preferably methyl, ethyl, propyl, butyl, pentyl, hexyl, heptyl, octyl, nonyl, decyl, undecyl, dodecyl, cycloalkyl, cyclooctyl, cyclododecyl, phenyl, substituted phenyl, 2-substituted phenyl, ortho-tolyl, 2,6-disubstitutedphenyl, and isomers thereof, including cyclohexyl).

In a preferred embodiment of the invention, R30 is selected from the group consisting of hydrogen, hydrocarbyls, substituted hydrocarbyls, and silyl groups (preferably alkyl, aryl, heteroaryl, and silyl groups, preferably methyl, ethyl, propyl, butyl, pentyl, hexyl, heptyl, octyl, nonyl, decyl, undecyl, dodecyl, phenyl, substituted phenyl, and isomers thereof, including cyclohexyl).

In a preferred embodiment of the invention, R2 contains 1 to 20 carbons, preferably R2 is selected from CH2, CH(aryl), CH(2-isopropylphenyl), CH(2,6-dimethylphenyl), CH(2,4-6-trimethylphenyl), CH(alkyl), CMe2, SiMe2, SiEt2, and SiPh2.

In a preferred embodiment of the invention, E and E* are, independently, carbon, silicon, or germanium (preferably carbon or silicon, preferably carbon). In a preferred embodiment of the invention, E and E* are both carbon.

In a preferred embodiment of the invention, each R12, R13, R6 and R7 is independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), R12 and R13 and/or R6 and R7 may be joined to form a saturated, substituted or unsubstituted hydrocarbyl ring, where the ring has 4, 5, 6, or 7 ring carbon atoms and where substitutions on the ring can join to form additional rings, or R12 and R13 and/or R6 and R7 may be joined to form a saturated heterocyclic ring, or a saturated substituted heterocyclic ring where substitutions on the ring can join to form additional rings.

In a preferred embodiment of the invention, at least one of R12 and R13 is a C1 to C100 (preferably C6 to C40, preferably C7 to C30, preferably C8 to C20) substituted or unsubstituted hydrocarbyl group (preferably aryl, phenyl, substituted phenyl, alkyl or aryl substituted phenyl, C2 to C30 alkyl or aryl substituted phenyl, 2-substituted phenyl, 2-isopropylphenyl, 2,4,6-trimethylphenyl, and the like).

In a preferred embodiment of the invention, at least one of R6 and R7 is a C1 to C100 (preferably C6 to C40, preferably C7 to C30, preferably C8 to C20) substituted or unsubstituted hydrocarbyl group (preferably aryl, phenyl, substituted phenyl, alkyl or aryl substituted phenyl, C2 to C30 alkyl or aryl substituted phenyl, 2-substituted phenyl, 2-isopropylphenyl, 2,4,6-trimethylphenyl, and the like).

In a preferred embodiment of the invention, R3, R4, and R5 are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups (R3 & R4 and/or R4 & R5) may be joined to form a substituted or unsubstituted hydrocarbyl or heterocyclic ring, where the ring has 5, 6, 7, or 8 ring atoms and where substitutions on the ring can join to form additional rings, preferably R3, R4, and R5 are independently selected from the group consisting of hydrogen, methyl, ethyl, propyl, butyl, pentyl, hexyl, heptyl, octyl, nonyl, decyl, undecyl, dodecyl, phenyl, substituted phenyl, and isomers thereof.

In a preferred embodiment of the invention, R8, R9, R10, and R11 are independently selected from the group consisting of hydrogen, hydrocarbyls, substituted hydrocarbyls, alkoxy, halogen, amino, and silyl, and the pairs of positions, and wherein adjacent R groups (R8 & R9, and/or R9 & R10, and/or R10 & R11) may be joined to form a saturated, substituted or unsubstituted hydrocarbyl or heterocyclic ring, where the ring has 5, 6, 7, or 8 ring carbon atoms and where substitutions on the ring can join to form additional rings, preferably R8, R9, R10, and R11 are independently selected from the group consisting of hydrogen, methyl, ethyl, propyl, butyl, pentyl, hexyl, heptyl, octyl, nonyl, decyl, undecyl, dodecyl, phenyl, substituted phenyl, and isomers thereof.

Preferably, the R groups above and other R groups mentioned hereafter, contain up to 30 carbon atoms, preferably no more than 30 carbon atoms, especially from 2 to 20 carbon atoms.

Preferably, M is Ti, Zr, or Hf and/or E and/or E* is carbon, with Zr or Hf based complexes being especially preferred.

In a preferred embodiment of the invention, R1 and R17 may be independently selected from phenyl groups that are variously substituted with between zero to five substituents that include F, Cl, Br, I, CF3, NO2, alkoxy, dialkylamino, aryl, and alkyl groups with between one to ten carbons.

In a preferred embodiment of the invention, each L may be independently selected from halide, alkyl, aryl, alkoxy, amido, hydrido, phenoxy, hydroxy, silyl, allyl, alkenyl, triflate, alkylsulfonate, arylsulfonate, and alkynyl. The selection of the leaving groups depends on the synthesis route adopted for arriving at the complex and may be changed by additional reactions to suit the later activation method in polymerization. For example, alkyl is preferred when using non-coordinating anions such as N,N-dimethylanilinium tetrakis(pentafluorophenyl)-borate or tris(pentafluorophenyl)borane. In another embodiment, two L groups may be linked to form a dianionic leaving group, for example, oxalate.

In another embodiment of the invention, each L' is independently selected from the group consisting of ethers, thioethers, amines, nitriles, imines, pyridines, and phosphines, preferably ethers.

In any embodiment of the invention described herein, M is preferably a Group 4 metal, preferably Zr or Hf.

In any embodiment of the invention described herein, E and/or E* is preferably carbon.

Preferably, in any embodiment of the invention described herein, R6 and R7 are the same.

In any embodiment of the invention described herein, R1, R3, R4, R5, and R17 may each contain no more than 30 carbon atoms.

In any embodiment of the invention described herein, E is carbon and R1 and R17 are independently selected from phenyl groups that are substituted with 0, 1, 2, 3, 4, or 5 substituents selected from the group consisting of F, Cl, Br, I, CF3, NO2, alkoxy, dialkylamino, hydrocarbyl, and substituted hydrocarbyls groups with from one to ten carbons.

In a preferred embodiment of the invention, the pyridyldiamido transition metal complex is represented by the Formula (A) above and at least one of R6 and R7 is a group containing from 1 to 100 (preferably 6 to 40, preferably 7 to 30) carbons.

In a preferred embodiment of the invention, the pyridyldiamido transition metal complex is represented by the Formula (A) above, and M is a Group 4 metal preferably Zr or Hf, preferably Hf.

In a preferred embodiment of the invention, the pyridyldiamido transition metal complex is represented by the Formula (B) above, and M is a Group 4 metal preferably Zr or Hf, preferably Hf.

In a preferred embodiment of the invention, the pyridyldiamido transition metal complex is represented by the Formula (A) above, and G2 is oxygen, and G1 and G3 are carbon atoms that are joined to each other by two to six additional atoms to form a cyclic structure.

In a preferred embodiment of the invention, the pyridyldiamido transition metal complex is represented by the Formula (B) above, and G2 is oxygen, and G1 and G3 are carbon atoms that are joined to each other by two to six additional atoms to form a cyclic structure.

In a preferred embodiment of the invention, the pyridyldiamido transition metal complex is represented by the Formula (A) above, and G2 is nitrogen, and G1 and G3 are carbon atoms that are joined to each other by two to six additional atoms to form a cyclic structure.

In a preferred embodiment of the invention, the pyridyldiamido transition metal complex is represented by the Formula (B) above, and G2 is nitrogen, and G1 and G3 are carbon atoms that are joined to each other by two to six additional atoms to form a cyclic structure.

In a preferred embodiment of the invention, the pyridyldiamido transition metal complex is represented by the Formula (A) above, and G2 is sulfur, and G1 and G3 are carbon atoms that are joined to each other by two to six additional atoms to form a cyclic structure.

In a preferred embodiment of the invention, the pyridyldiamido transition metal complex is represented by the Formula (B) above, and G2 is sulfur, and G1 and G3 are carbon atoms that are joined to each other by two to six additional atoms to form a cyclic structure.

In a preferred embodiment of the invention, the pyridyldiamido transition metal complex is represented by the Formula (C) above, and Q3 is C(H)C(H)C(H), R1 is 2,6-diisopropylphenyl, and R17 is phenyl.

In a preferred embodiment of the invention, the pyridyldiamido transition metal complex is represented by the Formula (D) above, R6 is H, R7 is a group containing between 1 to 100 (preferably 6 to 40, preferably 7 to 30) carbons, M is a Group 4 metal (preferably Zr or Hf, preferably Hf), and E is carbon.

In a preferred embodiment of the invention, the pyridyldiamido transition metal complex is represented by the Formula (A) above, and R1 is a 2,6-disubstituted aryl group where the substituents are selected from isopropyl, 3-pentyl, or cyclic aliphatic hydrocarbons containing between 4-20 carbons.

In a preferred embodiment of the invention, the pyridyldiamido transition metal complex is represented by the Formula (A) above, and Q1 is three atoms of a pyridine, imidazole, tetrahydrofuran, dioxane, dihydrothiazole, oxathiolane, tetrahydropyran, dihydrooxazole, or phosphinine group that is substituted at the adjacent positions.

In a preferred embodiment of the invention, the pyridyldiamido transition metal complex is represented by the Formula (A) above, and R2 is CH(aryl) with the aryl group containing between 7 and 20 carbon atoms.

In another aspect of the invention, there are provided various processes for synthesizing the complexes described herein.

The pyridyl diamine ligands described herein are generally prepared in multiple steps. One key step involves the preparation of a suitable "linker" group(s) containing both an aryl boronic acid (or acid ester) and an amine group. Examples of these include compounds of the general formula: 7-(boronic acid)-2,3-dihydro-1H-inden-1-(amine), 7-(boronic acid ester)-2,3-dihydro-1H-1-(amine), 7-(boronic acid)-1,2,3,4-tetrahydronaphthalen-1-(amine), 7-(boronic acid ester)-1,2, 34-tetrahydronaphthalen-1-(amine), which include various boronic acids, boronic acid esters, and amines. The linker groups may be prepared in high yield from arylhalide precursors containing amine functionality by first deprotonation of the amine group with 1.0 molar equivalents of n-BuLi, followed by transmetalation of an arylhalide with t-BuLi and subsequent reaction with a boron-containing reagent. This amine-containing linker is then coupled with a suitable pyridine containing species, such as 6-bromo-2-pyridinecarboxaldehyde. This coupling step typically uses a metal catalyst (e.g., Pd(PPh3)4) in less than 5 mol % loading. Following this coupling step, the new derivative, which can be described as amine-linker-pyridine-aldehyde, is then reacted with a second amine to produce the imine derivative amine-linker-pyridine-imine in a condensation reaction. This can then be reduced to the pyridyl diamine ligand by reaction with a suitable aryl anion, alkyl anion, or hydride source. This reaction is generally performed in etherial solvents at temperatures between −100° C. and 50° C. when aryllithium or alkyllithium reagents are employed. This reaction is generally performed in methanol at reflux when sodium cyanoborohydride is employed.

The preparation of pyridyl diamide metal complexes from pyridyl diamines may be accomplished using typical protonolysis and methylation reactions. In the protonolysis reaction the pyridyl diamine is reacted with a suitable metal reactant to produce a pyridyldiamide metal complex. A suitable metal reactant will feature a basic leaving group that will accept a proton from the pyridiyl diamine and then generally depart and be removed from the product. Suitable metal reactants include, but are not limited to, HfBn4 (Bn=CH2Ph), ZrBn4, TiBn4, ZrBn2Cl2(OEt2), HfBn2Cl2(OEt2)2, Zr(NMe2)2C12(dimethoxyethane), Hf(NMe2)2C12 (dimethoxyethane), Hf(NMe2)4, and Hf(NEt2)4. Pyridyldiamide metal complexes that contain metal-chloride groups, such as the PDA dichloride complex in Scheme 1 below, can be alkylated by reaction with an appropriate organometallic reagent. Suitable reagents include organolithium and organomagnesium, and Grignard reagents. The alkylations are generally performed in etherial or hydrocarbon solvents or solvent mixtures at temperatures typically ranging from −100° C. to 50° C.

The catalyst system typically comprises a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle, typically in a 10 wt % solution in toluene. The catalyst system employed in the present invention preferably Scheme 1

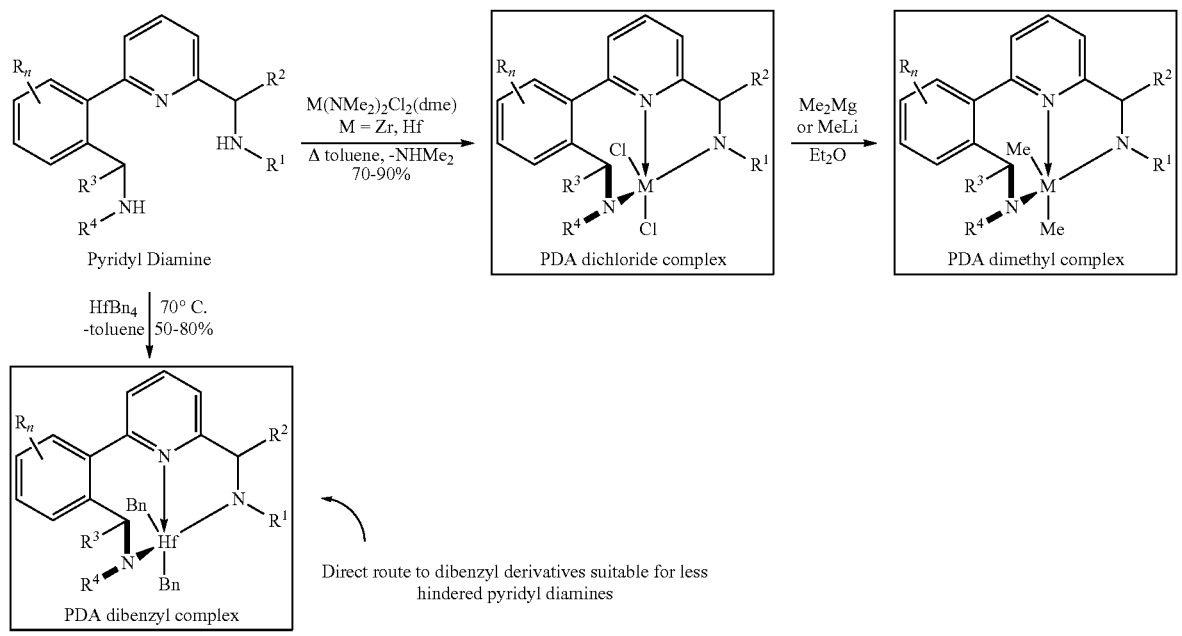

where in Scheme 1, R, $R^1$, $R^2$, $R^3$, $R^4$ are independently selected from the group consisting of H, hydrocarbyls (such as alkyls, aryls), substituted hydrocarbyls (such as heteroaryls), and silyl groups, and $R_n$ indicates hydrogen, hydrocarbyls, or substituted hydrocarbyls, which may be joined to form polycyclic aromatic ring and n is 1, 2, 3, or 4.

Figure 2:
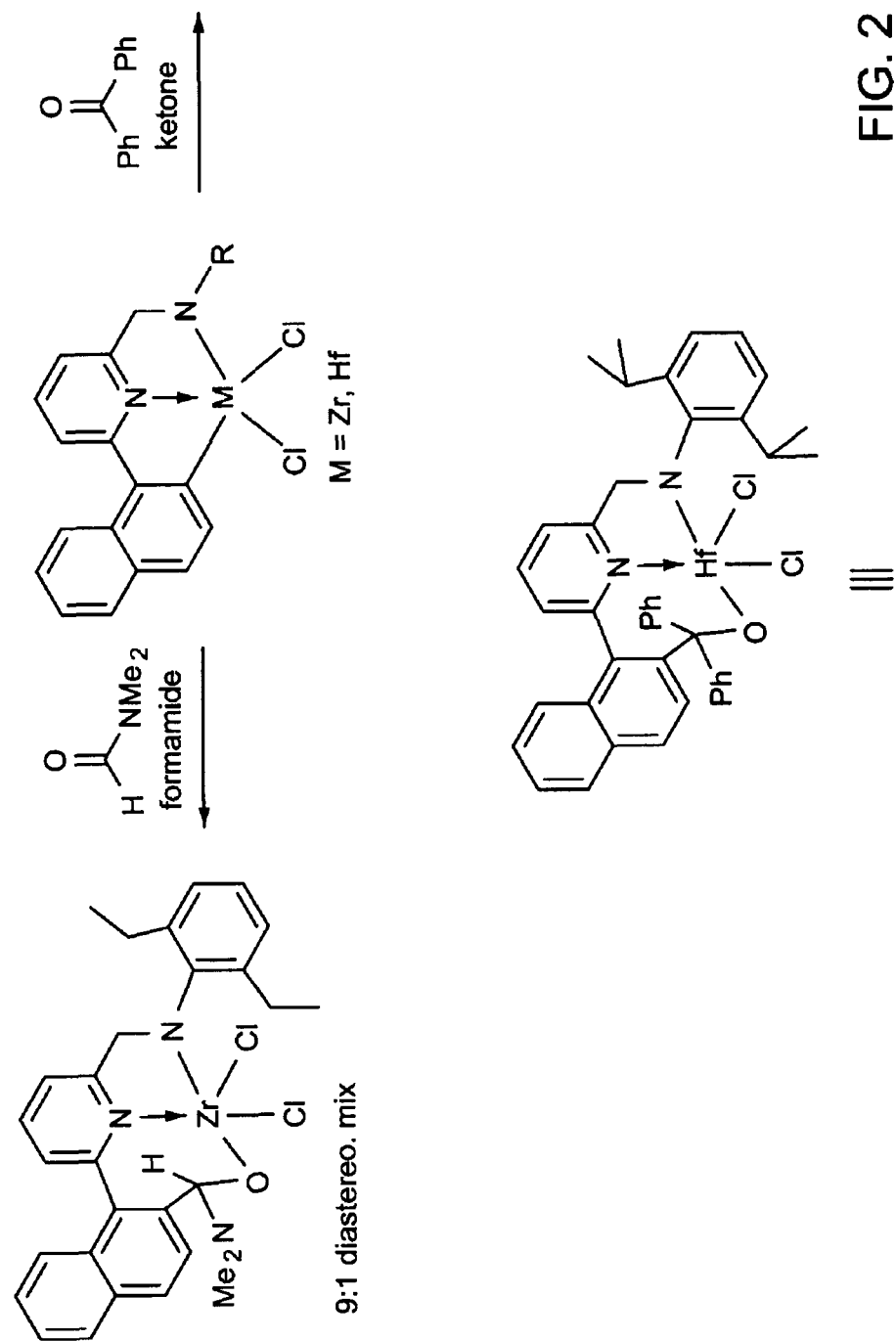
FIG. 2 is an illustration of insertion reactions involving benzophenone and N,N-dimethylformamide.
Figure 3:
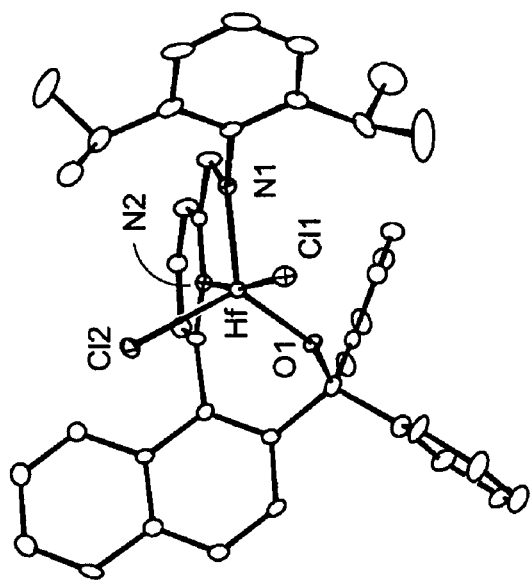
FIG. 3 illustrates the NMR spectra for the diasterotopic methylene.
Figure 3:
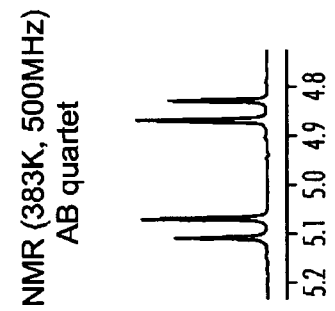
Figure 3:
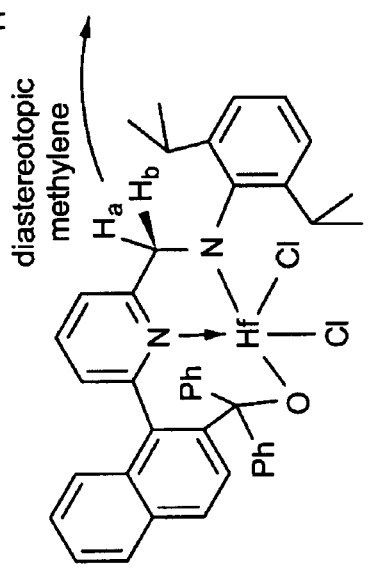

Another route to pyridyl diamide and other complexes of interest as catalysts involves the insertion of an unsaturated molecule into a covalent metal-carbon bond where the covalently bonded group is part of a multidentate ligand structure, such as that described by Boussie et al. in U.S. Pat. No. 6,750,345. The unsaturated molecule will generally have a carbon-X double or triple bond where X is a group 14 or group 15 or group 16 element. Examples of unsaturated molecules include alkenes, alkynes, imines, nitriles, ketones, aldehydes, amides, formamides, carbon dioxide, isocyanates, thioisocyanates, and carbodiimides. Examples showing the insertion reactions involving benzophenone and N,N-dimethylformamide are shown in FIG. 2.

Activators

After the complexes have been synthesized, catalyst systems may be formed by combining them with activators in any manner known from the literature, including by supporting them for use in slurry or gas phase polymerization. The catalyst systems may also be added to or generated in solution polymerization or bulk polymerization (in the monomer).

uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]+[NCA]− in which the N,N-dimethylanilinium (DMAH) cation reacts with a basic leaving group on the transition metal complex to form a transition metal complex cation and [NCA]−. The cation in the precursor may, alternatively, be trityl. Alternatively, the transition metal complex may be reacted with a neutral NCA precursor, such as B(C6F5)3, which abstracts an anionic group from the complex to form an activated species. Useful activators include N,N-dimethylanilinium tetrakis (pentafluorophenyl)borate (i.e., [PhNMe2H]B(C6F5)4) and N,N- dimethylanilinium tetrakis (heptafluoronaphthyl)borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

In an embodiment of the invention described herein, the non-coordinating anion activator is represented by the following formula (1):

$$(Z)_d^+ (A^{d-}) \qquad (1)$$

wherein Z is (L-H) or a reducible Lewis acid; L is a neutral Lewis base; H is hydrogen and (L-H)$^+$ is a Bronsted acid; A$^{d-}$ is a non-coordinating anion having the charge d−; and d is an integer from 1 to 3.

When Z is (L-H) such that the cation component is (L-H)d+, the cation component may include Bronsted acids such as protonated Lewis bases capable of protonating a moiety, such as an alkyl or aryl, from the catalyst precursor, resulting in a cationic transition metal species, or the activating cation (L-H)d+ is a Bronsted acid, capable of donating a proton to the catalyst precursor resulting in a transition metal cation, including ammoniums, oxoniums, phosphoniums, silyliums, and mixtures thereof, or ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, it may be represented by the formula: (Ar3C+), where Ar is aryl or aryl substituted with a heteroatom, or a C1 to C40 hydrocarbyl, the reducible Lewis acid may be represented by the formula: (Ph3C+), where Ph is phenyl or phenyl substituted with a heteroatom, and/or a C1 to C40 hydrocarbyl. In an embodiment, the reducible Lewis acid is triphenyl carbenium.

Embodiments of the anion component Ad− include those having the formula [Mk+Qn]d− wherein k is 1, 2, or 3; n is 1, 2, 3, 4, 5 or 6, or 3, 4, 5 or 6; n−k=d; M is an element selected from Group 13 of the Periodic Table of the Elements, or boron or aluminum, and Q is independently a hydride, bridged or unbridged dialkylamido, halide, alkoxide, aryloxide, hydrocarbyl radicals, said Q having up to 20 carbon atoms with the proviso that in not more than one occurrence is Q a halide, and two Q groups may form a ring structure. Each Q may be a fluorinated hydrocarbyl radical having 1 to 20 carbon atoms, or each Q is a fluorinated aryl radical, or each Q is a pentafluoryl aryl radical. Examples of suitable Ad− components also include diboron compounds as disclosed in U.S. Pat. No. 5,447,895, which is fully incorporated herein by reference.

In an embodiment in any of the NCA's represented by Formula 1 described above, the anion component Ad− is represented by the formula [M*k*+Q*n*]d*− wherein k* is 1, 2, or 3; n* is 1, 2, 3, 4, 5, or 6 (or 1, 2, 3, or 4); n*−k*=d*; M* is boron; and Q* is independently selected from hydride, bridged or unbridged dialkylamido, halogen, alkoxide, aryloxide, hydrocarbyl radicals, said Q* having up to 20 carbon atoms with the proviso that in not more than 1 occurrence is Q* a halogen.

This invention also relates to a method to polymerize olefins comprising contacting olefins (such as propylene) with a catalyst complex as described above and an NCA activator represented by the Formula (2):

$$R_n M^{**}(ArNHal)_{4-n} \qquad (2)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula 2 also comprises a suitable cation that is essentially non-interfering with the ionic catalyst complexes formed with the transition metal compounds, or the cation is $Z_d^+$ as described above.

In an embodiment in any of the NCA's comprising an anion represented by Formula 2 described above, R is selected from the group consisting of C1 to C30 hydrocarbyl radicals. In an embodiment, C1 to C30 hydrocarbyl radicals may be substituted with one or more C1 to C20 hydrocarbyl radicals, halide, hydrocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means C4 to C20 hydrocarbyl radicals; —SRa, —NRa2, and —PRa2, where each Ra is independently a monovalent C4 to C20 hydrocarbyl radical comprising a molecular volume greater than or equal to the molecular volume of an isopropyl substitution or a C4 to C20 hydrocarbyl substituted organometalloid having a molecular volume greater than or equal to the molecular volume of an isopropyl substitution.

In an embodiment in any of the NCA's comprising an anion represented by Formula 2 described above, the NCA also comprises cation comprising a reducible Lewis acid represented by the formula: (Ar3C+), where Ar is aryl or aryl substituted with a heteroatom, and/or a C1 to C40 hydrocarbyl, or the reducible Lewis acid represented by the formula: (Ph3C+), where Ph is phenyl or phenyl substituted with one or more heteroatoms, and/or C1 to C40 hydrocarbyls.

In an embodiment in any of the NCA's comprising an anion represented by Formula 2 described above, the NCA may also comprise a cation represented by the formula, (L-H)d+, wherein L is an neutral Lewis base; H is hydrogen; (L-H) is a Bronsted acid; and d is 1, 2, or 3, or (L-H)d+ is a Bronsted acid selected from ammoniums, oxoniums, phosphoniums, silyliums, and mixtures thereof.

Further examples of useful activators include those disclosed in U.S. Pat. Nos. 7,297,653 and 7,799,879, which are fully incorporated by reference herein.

In an embodiment, an activator useful herein comprises a salt of a cationic oxidizing agent and a noncoordinating, compatible anion represented by the Formula (3):

$$(OX^{e+})_d (A^{d-})_e \qquad (3)$$

wherein OX$^{e+}$ is a cationic oxidizing agent having a charge of e+; e is 1, 2 or 3; d is 1, 2 or 3; and A$^{d-}$ is a non-coordinating anion having the charge of d− (as further described above). Examples of cationic oxidizing agents include: ferrocenium, hydrocarbyl-substituted ferrocenium, Ag$^+$, or Pb$^{+2}$. Suitable embodiments of A$^{d-}$ include tetrakis(pentafluorophenyl)borate.

Activators useful in catalyst systems herein include: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, and the types disclosed in U.S. Pat. No. 7,297,653, which is fully incorporated by reference herein.

Suitable activators also include:

N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph3C+][B(C6F5)4−], [Me3NH+][B(C6F5)4−]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In an embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In an embodiment, two NCA activators may be used in the polymerization and the molar ratio of the first NCA activator to the second NCA activator can be any ratio. In an embodiment, the molar ratio of the first NCA activator to the second NCA activator is 0.01:1 to 10,000:1, or 0.1:1 to 1000:1, or 1:1 to 100:1.

In an embodiment of the invention, the NCA activator-to-catalyst ratio is a 1:1 molar ratio, or 0.1:1 to 100:1, or 0.5:1 to 200:1, or 1:1 to 500:1 or 1:1 to 1000:1. In an embodiment, the NCA activator-to-catalyst ratio is 0.5:1 to 10:1, or 1:1 to 5:1.

In an embodiment, the catalyst compounds can be combined with combinations of alumoxanes and NCA's (see for example, U.S. Pat. No. 5,153,157, U.S. Pat. No. 5,453,410, EP 0 573 120 B1, WO 94/07928, and WO 95/14044 which discuss the use of an alumoxane in combination with an ionizing activator, all of which are incorporated by reference herein).

In a preferred embodiment of the invention, when an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Supports

The complexes described herein may be supported (with or without an activator) by any method effective to support other coordination catalyst systems, effective meaning that the catalyst so prepared can be used for oligomerizing or polymerizing olefin(s) in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100% to 200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably, any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component; however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 m2/g, a pore volume of 0.1-4.0 cc/g and an average particle size of 10-500 μm. Some embodiments select a surface area of 50-500 m2/g, a pore volume of 0.5-3.5 cc/g, or an average particle size of 20-200 μm. Other embodiments select a surface area of 100-400 m2/g, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Invention catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. The complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization process used herein typically comprises contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 40 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of C2 to C10 alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a C3 to C20 α-olefin, and particularly a C3 to C12 α-olefin. Likewise, the present complexes are also particularly effective for the polymerization of propylene, either alone or in combination with at least one other olefinically unsaturated monomer, such as ethylene or a C4 to C20 α-olefin, and particularly a C4 to C20 α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1,3,5,5-trimethylhexene-1, and 5-ethylnonene-1.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture.

Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

In a preferred embodiment, the catalyst complexes described herein, preferably as represented by formula (A), (B), (C) or (D), preferably formula (C) or (D), are used in any polymerization process described above to produce ethylene homopolymers or copolymers, or propylene homopolymers or copolymers.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, tri-n-octyl aluminum, bis(diisobutylaluminum)oxide, modified methylalumoxane. (Useful modified methylalumoxane include cocatalyst type 3A (commercially available from Akzo Chemicals, Inc. under the trade name Modified Methylalumoxane type 3A) and those described in U.S. Pat. No. 5,041,584. Those scavenging compounds having bulky or C6-C20 linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [Me2HNPh]+[B(pfp)4]− or B(pfp)3 (perfluorophenyl=pfp=C6F5).

In a preferred embodiment, two or more complexes are combined with diethyl zinc in the same reactor with monomer. Alternately, one or more complexes are combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by Gel Permeation Chromatography. Preferred polymers produced herein may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:

1. A pyridyldiamido transition metal complex (preferably for use in alkene polymerization) represented by the formula: (A), (B), (C), or (D):

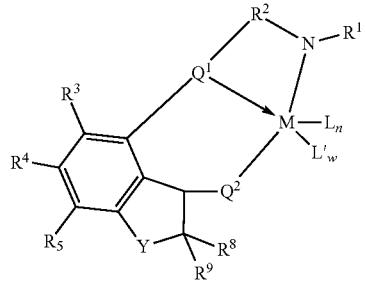

(A)

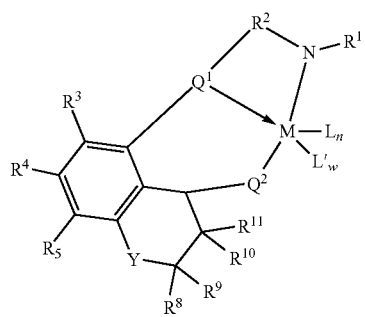

(B)

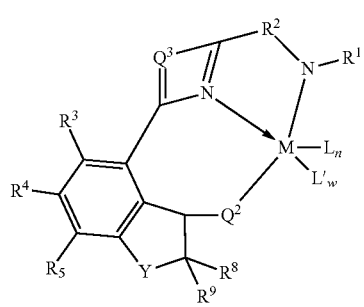

(C)

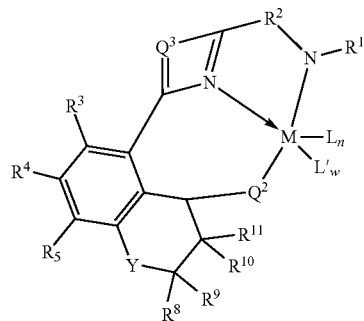

(D)

wherein:

M is a Group 3, 4, 5, 6, 7, 8, 9, 10, 11 or 12 metal;

$Q^1$ is a three atom bridge with the central of the three atoms being a group 15 or 16 element (said group 15 element may or may not be substituted with an $R^{30}$ group) represented by the formula: -$G^1$-$G^2$-$G^3$- where $G^2$ is a group 15 or 16 atom (said group 15 element may be substituted with a $R^{30}$ group), $G^1$ and $G^3$ are each a group 14, 15 or 16 atom (each group 14, 15 and 16 element may or may not be substituted with one or more $R^{30}$ groups), where $G^1$, $G^2$ and $G^3$, or $G^1$ and $G^2$, or $G^1$ and $G^3$, or $G^2$ and $G^3$ may form a singular or multi ring system;

each $R^{30}$ group is, independently, hydrogen or a $C_1$ to $C_{100}$ hydrocarbyl group or a silyl group;

$Q^2$ is —$NR^{17}$, —$PR^{17}$, or oxygen, where $R^{17}$ is selected from hydrogen, hydrocarbyls, substituted hydrocarbyls, silyls, and germyls;

$Q^3$ is -(TT)- or -(TTT)- where each T is carbon or a heteroatom, and said carbon or heteroatom may be unsubstituted or substituted with one or more $R^{30}$ groups that together with the "—C-$Q^3$=C—" fragment, forms a 5- or 6-membered cyclic group or a polycyclic group including the 5 or 6 membered cyclic group;

$R^1$ is selected from the group consisting of hydrocarbyls, and substituted hydrocarbyls, or silyl groups;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$, and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{10}$, $R^{11}$, $R^{12}$, and $R^{13}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^8$ & $R^9$, and/or $R^9$ & $R^{10}$, and/or $R^{10}$ & $R^{11}$ and/or $R^{12}$ & $R^{13}$) may be joined to form a saturated, substituted or unsubstituted hydrocarbyl or heterocyclic ring, where the ring has 5, 6, 7, or 8 ring carbon atoms and where substitutions on the ring can join to form additional rings;

$R^2$ is -$E(R^{12})(R^{13})$— with E being carbon, silicon, or germanium;

Y is selected from oxygen, sulfur, and -$E^*(R^6)(R^7)$—, with $E^*$ being carbon, silicon, or germanium;

L is an anionic leaving group, where the L groups may be the same or different and any two L groups may be linked to form a dianionic leaving group;

n is 0, 1, 2, 3, or 4;

L' is neutral Lewis base; and w is 0, 1, 2, 3 or 4.

2. The complex of paragraph 1, wherein M is Ti, Zr, or Hf.
3. The complex of paragraph 1 or 2, wherein $R^2$ is selected from $CH_2$, CH(aryl), CH(2-isopropylphenyl), CH(2,6-dimethylphenyl), CH(2,4-6-trimethylphenyl), CH(alkyl), $CMe_2$, $SiMe_2$, $SiEt_2$, and $SiPh_2$.
4. The complex of paragraph 1, 2, or 3, wherein T is C, O, S, or N.
5. The complex of paragraph 1, 2, 3, or 4, wherein E and E* are carbon and each $R^6$, $R^7$, $R^{12}$, and $R^{13}$ are a $C_1$ to $C_{30}$ substituted or unsubstituted hydrocarbyl group.
6. The complex of paragraph 1, 2, 3, 4, or 5, wherein E and E* are carbon and each $R^6$, $R^7$, $R^{12}$, and $R^{13}$ are a $C_6$ to $C_{30}$ substituted or unsubstituted aryl group.
7. The complex of paragraph 1, 2, 3, 4, 5, or 6, wherein $Q^2$ is —$NR^{17}$.
8. The complex of paragraph 1, 2, 3, 4, 5, 6, or 7, wherein E and E* are carbon and $R^1$ and $R^{17}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyl groups with from one to ten carbons.
9. The complex of any of paragraphs 1 to 8, wherein $Q^1$ is selected from:

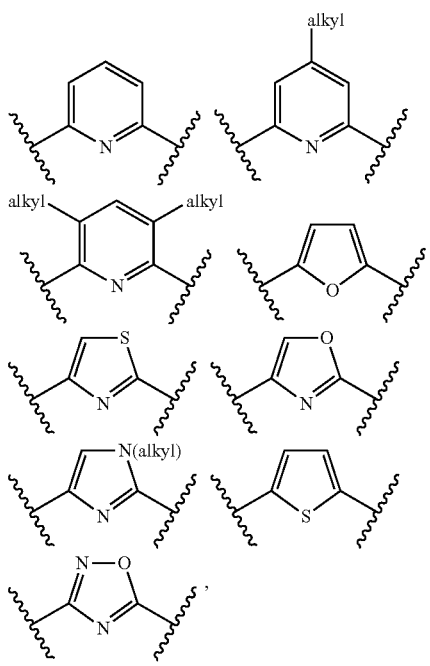

where the ⌇ symbols indicate the connections to $R^2$ and the aromatic ring, and alkyl is an alkyl group.
10. The complex of any of paragraphs 1 to 9, wherein each L is independently selected from the group consisting of halide, alkyl, aryl, alkoxy, amido, hydrido, phenoxy, hydroxy, silyl, allyl, alkenyl, triflate, alkylsulfonate, arylsulfonate, and alkynyl; and each L' is independently selected from the group consisting of ethers, thio-ethers, amines, nitriles, imines, pyridines, and phosphines.
11. The complex of any of paragraphs 1 to 10, wherein $Q^3$ is CHCHCH, CHCH, CHN(alkyl), CH—S, CHC(alkyl)CH, C(alkyl)CHC(alkyl), CH—O, or NO.
12. The complex of any of paragraphs 1 to 11, wherein the complex is represented by formula (A).

13. The complex of any of paragraphs 1 to 11, wherein the complex is represented by formula (B).
14. The complex of any of paragraphs 1 to 11, wherein the complex is represented by formula (C).
15. The complex of any of paragraphs 1 to 11, wherein the complex is represented by formula (D).
16. A catalyst system comprising an activator and the complex of any of paragraphs 1 to 15.
17. The catalyst system of paragraph 16, wherein the activator comprises an alumoxane.
18. The catalyst system of paragraph 16, wherein the activator comprises a non-coordinating anion.
19. The catalyst system of paragraph 18, wherein the activator comprises one or more of: trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F5)_4^-]$, $[Me_3NH^+][B(C_6F5)_4^-]$, 1-(4-(tris(pentafluorophenyl)borate)-2,3,5,6-tetrafluorophenyl)pyrrolidinium, tetrakis(pentafluorophenyl)borate, 4-(tris(pentafluorophenyl)borate)-2,3,5,6-tetrafluoropyridine, triphenylcarbenium tetraphenylborate, and triphenylcarbenium tetrakis-(2,3,4,6-tetrafluorophenyl)borate.
20. A polymerization process comprising contacting one or more alkene monomers with the catalyst system of paragraphs 16-19.
21. The process of paragraph 20 wherein the monomer comprises ethylene.
22. The process of paragraph 20 or 21 wherein the monomer comprises propylene.
23. The process of paragraph 20, 21, or 22 wherein the pyridyldiamido transition metal complex is supported.

EXPERIMENTAL

Preparation of N-[(6-bromopyridin-2-yl)methyl]-2,6-diisopropylaniline

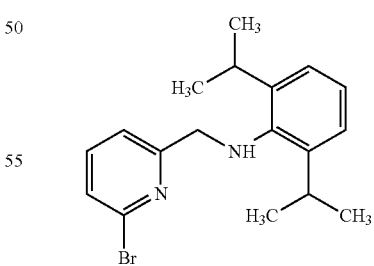

A solution of 85.0 g (457 mmol) of 6-bromopyridine-2-carbaldehyde and 80.9 g (457 mmol) of 2,6-diisopropylaniline in 1000 ml of ethanol was refluxed for 8 h. The obtained solution was evaporated to dryness, and the residue was recrystallized from 200 ml of methanol. In argon atmosphere, to thus obtained 113.5 g (329 mmol) of N-[(1E)-(6-bromopyridin-2-yl)methylene]-2,6-diisopropylaniline were added 33.16 g (526 mmol) of NaBH3CN, 9 ml of acetic acid and 1000 ml of methanol. This mixture was refluxed for 12 h, then cooled to room temperature, poured into 1000 ml of water, and crude product was extracted with 3×200 ml of ethyl acetate. The combined extract was dried over sodium sulfate and evaporated to dryness. The residue was purified by flash chromatography on silica gel 60 (40-63 um, eluent: hexane-ethyl acetate=10:1, vol.). Yield 104.4 g (66%) of a yellow oil. Anal. calc. for C18H23BrN2: C, 62.25; H, 6.68; N, 8.07. Found: C, 62.40; H, 6.87; N, 7.90. 1H NMR (CDCl3): δ 7.50 (m, 1H, 4-H in Py), 7.38 (m, 1H, 5-H in Py), 7.29 (m, 1H, 3-H in Py), 7.05-7.12 (m, 3H, 3,4,5-H in 2,6-iPr2C6H3), 4.18 (s, 2H, CH2NH), 3.94 (br.s, 1H, NH), 3.33 (sept, J=6.8 Hz, 2H, CHMe2), 1.23 (d, J=6.8 Hz, 12H, CHMe2).

Preparation of 7-bromoindan-1-ol

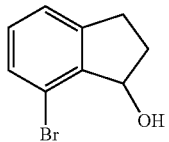

To a mixture of 100 g (746 mmol) of indan-1-ol, 250 ml (1.64 mol) of N,N,N',N'-tetramethylethylenediamine, and 3000 ml of pentane cooled to −20° C. 655 ml (1.64 mol) of 2.5M nBuLi in hexanes was added. After that the reaction mixture was refluxed for 12 h and then cooled to −80° C. Further on, 225 ml (1.87 mol) of 1,2-dibromotetrafluoroethane was added, and the resulting mixture was allowed to warm to room temperature. This mixture was stirred for 12 h, and then 100 ml of water was added. The resulting mixture was diluted with 2000 ml of water, and the organic layer was separated. The aqueous layer was extracted with 3×400 ml of toluene. The combined organic extract was dried over Na2SO4 and evaporated to dryness. The residue was distilled using a Kugelrohr apparatus, b.p. 120-140° C./1 mbar. The resulting yellow oil was dissolved in 50 ml of triethylamine, and the obtained solution added dropwise to a stirred solution of 49.0 ml (519 mmol) of acetic anhydride and 4.21 g (34.5 mmol) of 4-(dimethylamino)pyridine in 70 ml of triethylamine. The resulting mixture was stirred for 5 min, then 1000 ml of water was added, and stirring was continued for 12 h. After that the reaction mixture was extracted with 3×200 ml of ethyl acetate. The combined organic extract was washed with aqueous Na2CO3, dried over Na2SO4, and evaporated to dryness. The residue was purified by flash chromatography on silica gel 60 (40-63 um, eluent: hexane-ethyl acetate=30:1, vol.). The resulting ester was dissolved in 1000 ml of methanol, 50.5 g (900 mmol) of KOH was added, and this mixture was refluxed for 3 h. The reaction mixture was then cooled to room temperature and poured into 4000 ml of water. Crude product was extracted with 3×300 ml of dichloromethane. The combined organic extract was dried over Na2SO4 and evaporated to dryness. Yield 41.3 g (26%) of a white crystalline solid. Anal. Calc for C9H9BrO: C, 50.73; H, 4.26. Found: C, 50.85; H, 4.48. 1H NMR (CDCl3): δ 7.34 (d, J=7.6 Hz, 1H, 6-H); 7.19 (d, J=7.4 Hz, 1H, 4-H); 7.12 (dd, J=7.6 Hz, J=7.4 Hz, 1H, 5-H); 5.33 (dd, J=2.6 Hz, J=6.9 Hz, 1H, 1-H), 3.18-3.26 (m, 1H, 3- or 3'-H), 3.09 (m, 2H, 3,3'-H); 2.73 (m, 2H, 2,2'-H).

Preparation of 7-bromoindan-1-one

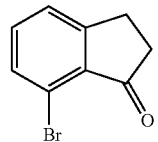

To a solution of 37.9 g (177 mmol) of 7-bromoindan-1-ol in 3500 ml of dichloromethane 194 g (900 mmol) of pyridinium chlorochromate was added. The resulting mixture was stirred at room temperature for 5 h, then passed through a silica gel pad (500 ml), and the elute was evaporated to dryness. Yield 27.6 g (74%) of a white crystalline solid. Anal. Calc for C9H7BrO: C, 51.22; H, 3.34. Found: C, 51.35; H, 3.41. 1H NMR (CDCl3): δ 7.51 (m, 1H, 6-H); 7.36-7.42 (m, 2H, 4,5-H); 3.09 (m, 2H, 3,3'-H); 2.73 (m, 2H, 2,2'-H).

Preparation of 7-bromo-N-phenyl-2,3-dihydro-1H-inden-1-amine

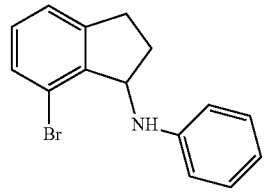 [SMILES: Brc1cccc2c1C(Nc1ccccc1)CC2]

To a stirred solution of 10.4 g (112 mmol) of aniline in 60 ml of toluene 5.31 g (28.0 mmol) of TiCl4 was added for 30 min at room temperature in argon atmosphere. The resulting mixture was stirred at 90° C. for 30 min followed by an addition of 6.00 g (28.0 mmol) of 7-bromoindan-1-one. The resulting mixture was stirred for 10 min at 90° C., poured into 500 ml of water, and crude product was extracted with 3×100 ml of ethyl acetate. The organic layer was separated, dried over Na2SO4, and then evaporated to dryness. The residue was crystallized from 10 ml of ethyl acetate at −30° C. The resulting solid was separated and dried in vacuum. After that it was dissolved in 100 ml of methanol, 2.70 g (42.9 mmol) of NaBH3CN and 0.5 ml of glacial acetic acid was added. The resulting mixture was refluxed for 3 h in argon atmosphere. The resulting mixture was cooled to room temperature and then evaporated to dryness. The residue was diluted with 200 ml of water, and crude product was extracted with 3×50 ml of ethyl acetate. The combined organic extract was dried over Na2SO4 and evaporated to dryness. The residue was purified by flash chromatography on silica gel 60 (40-63 um, eluent: hexane-ethyl acetate-triethylamine=100:10:1, vol.). Yield 5.50 g (68%) of a yellow oil. Anal. calc. for C15H14BrN: C, 62.52; H, 4.90; N, 4.86. Found: C, 62.37; H, 5.05; N, 4.62. 1H NMR (CDCl3): δ 7.38 (m, 1H, 6-H in indane); 7.22 (m, 3H, 3,5-H in phenyl and 4-H in indane); 7.15 (m, 1H, 5-H in indane); 6.75 (m, 1H, 4-H in indane); 6.69 (m, 2H, 2,6-H in phenyl); 4.94 (m, 1H, 1-H in indane); 3.82 (br.s, 1H, NH);

3.17-3.26 (m, 1H, 3- or 3'-H in indane); 2.92-2.99 (m, 2H, 3'- or 3-H in indane); 2.22-2.37 (m, 2H, 2,2'-H in indane).

Preparation of N-phenyl-7-(4,4,5,5-tetramethyl-1,3,2-dioxaborolan-2-yl)-2,3-dihydro-1H-inden-1-amine

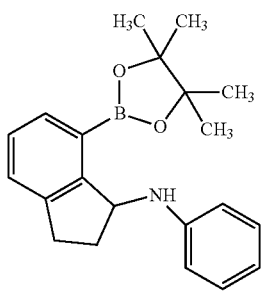 [SMILES: CC1(C)OB(c2cccc3c2C(Nc2ccccc2)CC3)OC1(C)C]

To a solution of 2.50 g (8.70 mmol) of 7-bromo-N-phenyl-2,3-dihydro-1H-inden-1-amine in 50 ml THF 3.50 ml (8.70 mmol) of 2.5M nBuLi in hexanes was added at −80° C. in argon atmosphere. The reaction mixture was then stirred for 1 h at this temperature. Further on, 11.1 ml (17.8 mmol) of 1.7M tBuLi in pentane was added, and the reaction mixture was stirred for 1 h. Then, 3.23 g (17.4 mmol) of 2-isopropoxy-4,4,5,5-tetramethyl-1,3,2-dioxaborolane was added. After that the cooling bath was removed, and the resulting mixture was stirred for 1 h at room temperature. To the formed mixture 10 ml of water was added, and the resulting mixture was evaporated to dryness. The residue was diluted with 200 ml of water, and the title product was extracted with 3×50 ml of ethyl acetate. The combined organic extract was dried over Na2SO4 and evaporated to dryness. Yield 2.80 g (96%) of a light yellow oil. Anal. calc. For C21H26BNO2: C, 75.24; H, 7.82; N, 4.18. Found: C, 75.40; H, 8.09; N, 4.02. 1H NMR (CDCl3): δ 7.63 (m, 1H, 6-H in indane); 7.37-7.38 (m, 1H, 4-H in indane); 7.27-7.30 (m, 1H, 5-H in indane); 7.18 (m, 2H, 3,5-H in phenyl); 6.65-6.74 (m, 3H, 2,4,6-H in phenyl); 5.20-5.21 (m, 1H, 1-H in indane); 3.09-3.17 (m, 1H, 3- or 3'-H in indane); 2.85-2.92 (m, 1H, 3'- or 3-H in indane); 2.28-2.37 (m, 1H, 2- or 2'-H in indane); 2.13-2.19 (m, 1H, 2'- or 2-H in indane); 1.20 (s, 6-H, 4,5-Me in BPin); 1.12 (s, 6H, 4',5'-Me in BPin).

Preparation of 7-(6-(((2,6-diisopropylphenyl)amino)methyl)pyridin-2-yl)-N-phenyl-2,3-dihydro-1H-inden-1-amine

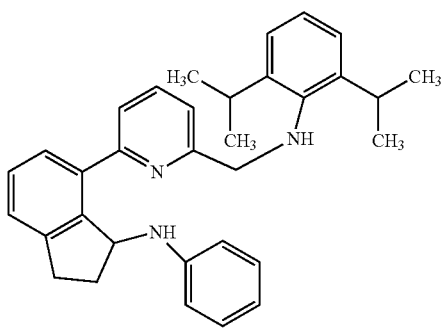 [SMILES: CC(C)c1cccc(C(C)C)c1NCc1cccc(-c2cccc3c2C(Nc2ccccc2)CC3)n1]

A solution of 2.21 g (21.0 mmol) of Na2CO3 in a mixture of 80 ml of water and 25 ml of methanol was purged with argon for 30 min. The obtained solution was added to a mixture of 2.80 g (8.40 mmol) of N-phenyl-7-(4,4,5,5-tetramethyl-1,3,2-dioxaborolan-2-yl)-2,3-dihydro-1H-inden-1-amine, 2.90 g (8.40 mmol) of N-[(6-bromopyridin-2-yl)methyl]-2,6-diisopropylaniline, 0.48 g (0.40 mmol) of Pd(PPh3)4, and 120 ml of toluene. This mixture was stirred for 12 h at 70° C., then cooled to room temperature. The organic layer was separated, the aqueous layer was extracted with 3×50 ml of ethyl acetate. The combined organic extract was washed with brine, dried over Na2SO4 and evaporated to dryness. The residue was purified by flash chromatography on silica gel 60 (40-63 um, eluent: hexane-ethyl acetate-triethylamine=100:5:1, vol.). Yield 2.00 g (50%) of a yellow oil. Anal. calc. For C33H37N3: C, 83.33; H, 7.84; N, 8.83. Found: C, 83.49; H, 7.66; N, 8.65. 1H NMR (CDCl3): δ 7.56-7.61 (m, 3H, 6-H in indane and 4.5-H in Py); 7.46-7.51 (m, 2H, 3,5-H in phenyl); 7.14-7.16 (m, 1H, 4-H in indane); 7.08-7.12 (m, 5H, 3-H in Py, 3,4,5-H in 2,6-diisopropylphenyl and 5-H in indane); 6.65 (m, 1H, 4-H in phenyl); 6.53 (m, 2H, 2,6-H in phenyl); 5.21-5.22 (m, 1H, 1-H in indane); 3.95-4.15 (m, 4H, CH2NH and NH-phenyl and NH-2,6-diisopropylphenyl); 3.31 (sept, J=6.8 Hz, 2H, CH in 2,6-diisopropylphenyl); 3.16-3.24 (m, 1H, 3- or 3'-H in indane); 2.91-2.97 (m, 1H, 3'- or 3-H in indane); 2.21-2.37 (m, 2H, 2,2'-H in indane); 1.19-2.21 (m, 12H, CH3 in 2,6-diisopropylaniline).

Preparation of Complex 1

Toluene (5 mL) was added to 7-(6-(((2,6-diisopropylphenyl)amino)methyl)pyridin-2-yl)-N-phenyl-2,3-dihydro-1H-inden-1-amine (0.296 g, 0.623 mmol) and Hf(NMe2)2Cl2(dme) (0.267 g, 0.623 mmol) to form a clear colorless solution. The mixture was loosely capped with aluminum foil and heated to 95° C. for 3 hours. The mixture was then evaporated to a solid and washed with Et2O (5 mL) to afford 0.432 g of the presumed (pyridyldiamide) HfCl2 complex. This was dissolved in CH2Cl2 (5 mL) and cooled to −500° C. A Et20 solution of dimethylmagnesium (3.39 mL, 0.747 mmol) was added dropwise and the mixture was allowed to warm to ambient temperature. After 30 minutes the volatiles were removed by evaporation and the residue was extracted with CH2Cl2 (10 mL) and filtered. The solution was concentrated to 2 mL and pentane (4 mL) was added. Cooling to −10° C. overnight afforded colorless crystals that were isolated and dried under reduced pressure. Yield=0.41 g, 92%. 1H NMR (CD2Cl2, 400 MHz): 8.00 (t, 1H), 6.85-7.65 (13H), 5.06 (d, 1H), 4.91 (dd, 1H), 4.50 (d, 1H), 3.68 (sept, 1H), 3.41 (m, 1H), 2.85 (m, 1H), 2.61 (sept, 1H), 2.03 (m, 1H), 1.85 (m, 1H), 1.30 (m, 2H), 1.14 (d, 3H), 1.06 (d, 3H), 0.96 (d, 3H), 0.68 (3, 3H), −0.48 (s, 3H), −0.84 (s, 3H).

Preparation of 8-bromo-1,2,3,4-tetrahydronaphthalen-1-ol

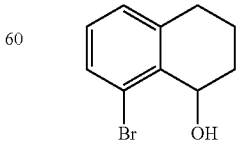

To a mixture of 78.5 g (530 mmol) of 1,2,3,4-tetrahydronaphthalen-1-ol, 160 ml (1.06 mol) of TMEDA, and 3000 ml of pentane cooled to −20° C. 435 ml (1.09 mol) of 2.5M nBuLi in hexanes was added dropwise. The obtained mixture was refluxed for 12 h. To the resulting mixture cooled to −80° C. 160 ml (1.33 mol) of 1,2-dibromotetrafluoroethane was added, and this mixture was allowed to warm to room temperature and then stirred for 12 h at this temperature. After that 100 ml of water was added. The resulting mixture was diluted with 2000 ml of water, and the organic layer was separated. The aqueous layer was extracted with 3×400 ml of toluene. The combined organic extract was dried over Na2SO4 and evaporated to dryness. The residue was distilled using the Kugelrohr apparatus, b.p. 150-160° C./1 mbar. The resulting yellow oil was dissolved in 100 ml of triethylamine, and the obtained solution was added dropwise to a stirred solution of 71.0 ml (750 mmol) of acetic anhydride and 3.00 g (25.0 mmol) of DMAP in 105 ml of triethylamine. The resulting mixture was stirred for 5 min, then 1000 ml of water was added, and the obtained mixture was stirred for 12 h. After that the reaction mixture was extracted with 3×200 ml of ethyl acetate. The combined organic extract was washed with aqueous Na2CO3, dried over Na2SO4, and evaporated to dryness. The residue was purified by flash chromatography on silica gel 60 (40-63 um, eluent: hexane-ethyl acetate=30:1, vol.). The resulting acetate was dissolved in 1500 ml of methanol, 81.0 g (1.45 mol) of KOH was added, and the obtained mixture was refluxed for 3 h. The reaction mixture was then cooled to room temperature and poured into 4000 ml of water, and the title product was extracted with 3×300 ml of dichloromethane. The combined organic extract was dried over Na2SO4 and then evaporated to dryness. Yield 56.0 g (47%) of a white crystalline solid. Anal. Calc for C10H11BrO: C, 52.89; H, 4.88. Found: C, 53.01; H, 4.75. 1H NMR (CDCl3): δ 7.38-7.41 (m, 1H, 7-H); 7.03-7.10 (m, 2H, 5,6-H); 5.00 (m, 1H, 1-H); 2.81-2.87 (m, 1H, 4- or 4'-H), 2.70-2.74 (m, 1H, 4'- or 4-H), 2.56 (br.s., 1H, OH), 2.17-2.21 (m, 1H, 2- or 2'-H), 1.74-1.79 (m, 2H, 3,3'-H).

Preparation of 8-bromo-3,4-dihydronaphthalen-1(2H)-one

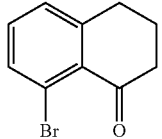 [SMILES: O=C1CCCc2cccc(Br)c21]

To a solution of 56.0 g (250 mmol) of 8-bromo-1,2,3,4-tetrahydronaphthalen-1-ol in 3500 ml of dichloromethane 265 g (1.23 mol) of PCC was added. The resulting mixture was stirred at room temperature for 5 h, then passed through a silica gel pad (500 ml), and evaporated to dryness. Yield 47.6 g (88%) of a colorless solid. Anal. Calc for C10H9BrO: C, 53.36; H, 4.03. Found: C, 53.44; H, 4.19. 1H NMR (CDCl3): δ 7.53 (m, 1H, 7-H); 7.18-7.22 (m, 2H, 5,6-H); 2.95 (t, J=6.1 Hz, 2H, 4,4'-H); 2.67 (t, J=6.6 Hz, 2H, 2,2'-H); 2.08 (qv, J=6.1 Hz, J=6.6 Hz, 2H, 3,3'-H).

Preparation of 8-bromo-N-(o-tolyl)-1,2,3,4-tetrahydronaphthalen-1-amine

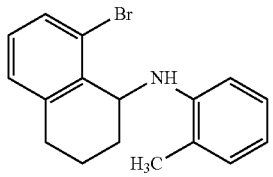 [SMILES: Cc1ccccc1NC1CCCc2cccc(Br)c21]

To a stirred solution of 57.1 g (533 mmol) of 2-methylaniline in 300 ml of toluene 25.3 g (133 mmol) of TiCl4 was added dropwise for 30 min at room temperature in argon atmosphere. The resulting mixture was stirred for 30 min at 90° C. followed by an addition of 30.0 g (133.0 mmol) 8-bromo-3,4-dihydronaphthalen-1(2H)-one. This mixture was stirred for 10 min at 90° C., poured into 500 ml of water, and the product was extracted with 3×200 ml of ethyl acetate. The combined organic extract was dried over Na2SO4 and evaporated to dryness. The residue was re-crystallized from 50 ml of ethyl acetate. The obtained solid was dissolved in 600 ml of methanol, 15.4 g (244 mmol) of NaBH3CN and 5 ml of acetic acid were added in argon atmosphere. The resulting mixture was refluxed for 3 h, then cooled to room temperature, and evaporated to dryness. The residue was diluted with 500 ml of water, and crude product was extracted with 3×200 ml of ethyl acetate. The combined organic extract was dried over Na2SO4 and evaporated to dryness. The residue was re-crystallized from 400 ml of methanol. Yield 33.2 g (79%) of a yellow crystalline powder. Anal. Calc. for C17H18BrN: C, 64.57; H, 5.74; N, 4.43. Found: C, 64.69; H, 5.82; N, 4.55. 1H NMR (CDCl3): δ 7.45 (m, 1H, 7-H in tetrahydronaphtalene); 7.19 (m, 1H, 6-H in tetrahydronaphtalene); 7.08-7.14 (m, 3H, 5-H in tetrahydronaphtalene and 3,5-H in 2-methylphenyl); 6.86 (m, 1H, 6-H in 2-methylphenyl); 6.68 (m, 1H, 4-H in 2-methylphenyl); 4.78 (m, 1H, 4-H in 2-methylphenyl); 3.51 (br.s, 1H, NH); 2.86-2.92 (m, 1H, 4- or 4'-H in tetrahydronaphtalene); 2.72-2.81 (m, 1H, 4'- or 4-H in tetrahydronaphtalene); 2.30-2.34 (m, 1H, 3- or 3'-H in tetrahydronaphtalene); 2.06 (s, 3H, CH3 in 2-methylphenyl); 1.85-1.97 (m, 1H, 3'- or 3-H in tetrahydronaphtalene); 1.77-1.81 (m, 1H, 2- or 2'-H in tetrahydronaphtalene); 1.59-1.67 (m, 1H, 2'- or 2-H in tetrahydronaphtalene).

Preparation of 8-(4,4,5,5-tetramethyl-1,3,2-dioxaborolan-2-yl)-N-(o-tolyl)-1,2,3,4-tetrahydronaphthalen-1-amine

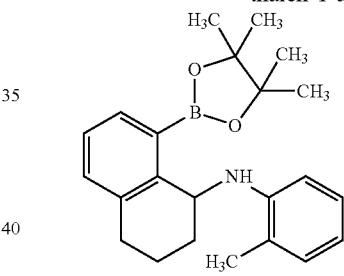

To a solution of 30.8 g (97.5 mmol) (8-bromo-1,2,3,4-tetrahydronaphthalen-1-yl)(2-methylphenyl)amine in 500 ml THF 39.0 ml (97.5 mmol) of 2.5M nBuLi in hexanes was added at −80° C. in argon atmosphere. The resulting mixture and stirred for 1 h at this temperature, and then 125 ml (200 mmol) of 1.7M tBuLi in pentane was added. The obtained mixture was stirred for 1 h at the same temperature. Further on, 36.3 g (195 mmol) of 2-isopropoxy-4,4,5,5-tetramethyl-1,3,2-dioxaborolane was added. After that the cooling bath was removed, and the resulting mixture was stirred for 1 h at room temperature. Then, 10 ml of water was added, and this mixture was evaporated to dryness. The residue was diluted with 500 ml of water, and the title product was extracted with 3×200 ml of ethyl acetate. The combined organic extract was dried over Na2SO4 and evaporated to dryness. Yield 24.8 g (70%) of a yellow oil. Anal. Calc. For C23H30BNO2: C, 76.04; H, 8.32; N, 3.86. Found: C, 76.29; H, 8.60; N, 3.59. 1H NMR (CDCl3): δ 7.68-7.69 (m, 1H, 7-H in tetrahydronaphtalene); 7.24-7.33 (m, 3H, 5,6-H in tetrahydronaphtalene and 5-H in 2-methylphenyl); 7.13 (m, 1H, 3-H in 2-methylphenyl); 7.04 (m, 1H, 6-H in 2-methylphenyl); 6.74-6.77 (m, 1H, 4-H in 2-methylphenyl); 5.38-5.39 (m, 1H, 1-H in tetrahydronaphtalene); 3.78 (m, 1H, NH); 2.85-3.02 (m, 2H, 4-H in tetrahydronaphtalene); 2.21-2.26 (m, 1H, 3- or 3'-H in tetrahydronaphtalene); 2.12 (s, 3H, CH3 in 2-methylphenyl); 1.81-2.00 (m, 3H, 3'- or 3-H and 2-H in tetrahydronaphtalene); 1.20 (s, 6H, CH3 in BPin); 1.13 (s, 6H, CH3 in BPin).

Preparation of 8-(6-(((2,6-diisopropylphenyl)amino)methyl)pyridin-2-yl)-N-phenyl-1,2,3,4-tetrahydronaphthalen-1-amine

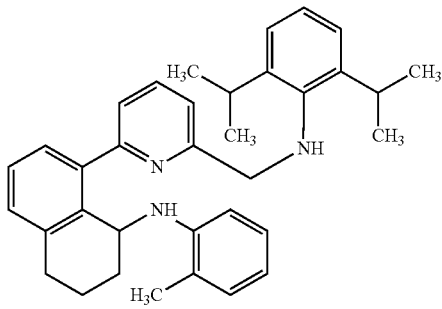 [SMILES: Cc1ccccc1NC1CCCc2cccc(-c3cccc(CNc4c(C(C)C)cccc4C(C)C)n3)c21]

A solution of 3.60 g (34.0 mmol) of Na2CO3 in a mixture of 150 ml of water and 45 ml of methanol was purged with argon for 30 min. The obtained solution was added to a mixture of 5.00 g (14.0 mmol) of N-(2-methylphenyl)-8-(4,4,5,5-tetramethyl-1,3,2-dioxaborolan-2-yl)-1,2,3,4-tetrahydronaphthalen-1-amine, 4.85 g (14.0 mmol) of N-[(6-bromopyridin-2-yl)methyl]-2,6-diisopropylaniline, 0.80 g (0.70 mmol) of Pd(PPh3)4, and 180 ml of toluene in argon atmosphere. This mixture was stirred for 12 h at 70° C. and then cooled to room temperature. The organic layer was separated, the aqueous layer was extracted with 3×50 ml of ethyl acetate. The combined organic extract was washed with brine, dried over Na2SO4, and evaporated to dryness. The residue was purified by flash chromatography on silica gel 60 (40-63 um, eluent: hexane-ethyl acetate-triethylamine=100:10:1, vol.). Yield 2.50 g (36%) of a yellow oil. Anal. Calc. for C35H41N3: C, 83.45; H, 8.20; N, 8.34. Found: C, 83.69; H, 8.08; N, 8.13.1H NMR (CDCl3): δ 7.62-7.63 (m, 1H, 7-H in tetrahydronaphtalene); 7.55-7.58 (m, 1H, 4-H in Py); 7.52-7.54 (m, 1H, 3-H in Py); 7.41-7.44 (m, 1H, 6-H in tetrahydronaphtalene); 7.37-7.39 (m, 1H, 5-H in Py); 7.15-7.16 (m, 1H, 5-H in tetrahydronaphtalene); 7.03-7.10 (m, 4H, 3,4,5-H in 2,6-diisopropylphenyl and 5-H in 2-methylphenyl); 6.93 (m, 1H, 3-H in 2-methylphenyl); 6.70 (m, 1H, 6-H in 2-methylphenyl); 6.59 (m, 1H, 4-H in 2-methylphenyl); 5.35 (m, 1H, 1-H in tetrahydronaphtalene); 3.94-4.03 (m, 2H, CH2); 3.92-3.94 (m, 1H, 4- or 4'-H in tetrahydronaphtalene); 3.68-3.70 (m, 1H, 4'- or 4-H in tetrahydronaphtalene); 3.30 (sept, J=6.8 Hz, 2H, CH in 2,6-diisopropylphenyl); 3.16-3.24 (m, 1H, 3- or 3'-H in tetrahydronaphtalene); 2.92-3.00 (m, 1H, 3'- or 3-H in tetrahydronaphtalene); 2.38-2.47 (m, 1H, 2- or 2'-H in tetrahydronaphtalene); 2.14-2.22 (m, 1H, 2'- or 2-H in tetrahydronaphtalene); 1.75 (s, 3H, CH3 in 2-methylphenyl); 1.18-1.22 (m, 12H, CH3 in 2,6-diisopropylphenyl).

Preparation of Complex 2

Toluene (8 mL) was added to 8-(6-(((2,6-diisopropylphenyl)amino)methyl)pyridin-2-yl)-N-phenyl-1,2,3,4-tetrahydronaphthalen-1-amine (0.214 g, 0.501 mmol) and Hf(NMe2)2Cl2(dme) (0.214 g, 0.501 mmol) to form a pale yellow solution. The mixture was loosely capped with aluminum foil and heated to 95° C. for 3 hours. The mixture was then evaporated to a solid and washed with Et20 (5 mL) to afford 0.314 g of the presumed (pyridyldiamide) HfCl2 complex. This was dissolved in CH2Cl2 (5 mL) and cooled to −50° C. An Et20 solution of dimethylmagnesium (1.53 mL, 0.481 mmol) was added dropwise and the mixture was allowed to warm to ambient temperature. After 30 minutes the volatiles were removed by evaporation and the residue was extracted with CH2Cl2 (8 mL) and filtered. Evaporation afforded a solid that was washed with pentane (4 mL) and dried under reduced pressure to afford complex 2. Yield=0.28 g, 79%. 1H NMR (CD2Cl2, 400 MHz): 8.02 (t, 1H), 6.85-7.65 (12H), 5.16 (d, 1H), 4.72 (br, 1H), 5.60 (br d, 1H), 3.68 (sept, 1H), 3.50 (m, 1H), 2.85 (m, 1H), 2.59 (br, 1H), 2.2 (br, 2H), 1.85 (m, 1H), 1.55 (m, 1H), 1.10 (m, 6H), 0.95 (d, 3H), 0.4 (d, 3H), −0.63 (s, 3H), −0.90 (s, 3H).

Complex 3 (comparative) was prepared as described in U.S. Pat. No. 8,394,902. Complex 4 (comparative) was prepared according to the general procedures described in U.S. Pat. No. 8,394,902.

1

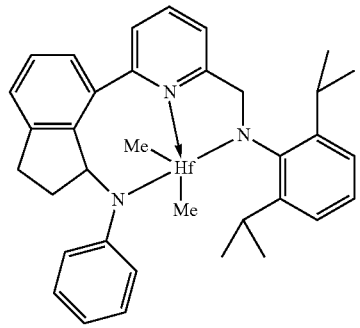

2

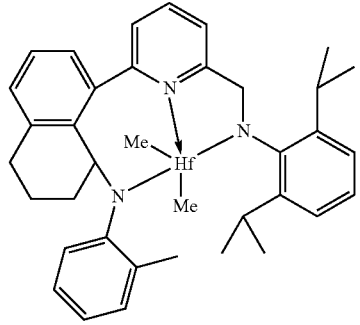

3

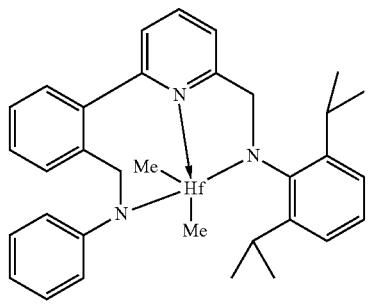

(comparative)

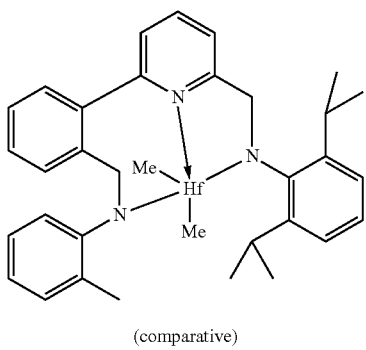

(comparative)

Polymerizations Examples

Shown in Table 1 are propylene polymerization data at 70° C. temperature using complexes 1-2 (runs 1-4) and comparative complex 4 (runs 5-6). From this data it is apparent that the catalysts formed by the activation of complexes 1 and 2 have significantly higher activity than the comparative example. On average, the catalyst produced from complex 1 was 38% more active than the catalyst formed from complex 4. Similarly, the catalyst produced from complex 2 was 42% more active than the catalyst formed from complex 4. The presence of the tetrahydronaphthalene group also leads to an increase in the melting point of the polypropylene produced by about 2° C. This is observed by comparing the melting point of polypropylene produced by complex 2 (runs 3-4) to that produced by complex 4 (runs 5-6).

Shown in Table 2 are propylene polymerization data at 85° C. temperature using complexes 1-2 (runs 7-10) and comparative complexes 3 (run 11) and 4 (runs 12-13). From this data it is apparent that the catalysts formed by the activation of complexes 1 and 2 have significantly higher activity than the comparative examples. On average, the catalyst produced from complex 1 was 49% more active than the catalyst formed from complex 4. Similarly, the catalyst produced from complex 2 was 42% more active than the catalyst formed from complex 4. Relative to the catalyst produced from complex 3 the inventive catalysts from complexes 1 and 2 showed improvements in activity of 252% and 236%, respectively. The presence of the tetrahydronaphthalene group also leads to an increase in the melting point of the polypropylene produced by about 2° C. This is observed by comparing the melting point of polypropylene produced by complex 2 (runs 9-10) to that produced by complex 4 (runs 12-13). Similarly, the presence of the dihydroindene group also leads to an increase in the melting point of the polypropylene produced by about 12° C. This is observed by comparing the melting point of polypropylene produced by complex 1 (runs 7-8) to that produced by complex 3 (run 11).

General Polymerization Procedures

Unless stated otherwise the propylene homopolymerizations were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pp. 4306-4317, each of which is fully incorporated herein by reference for US purposes. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. Then solvent (typically isohexane) was added to bring the total reaction volume, including the subsequent additions, to 4 mL. Propylene gas was introduced and the reactor vessels were heated to their set temperature. At this time scavenger and/or co-catalyst and/or a chain transfer agent, such as tri-n-octylaluminum in toluene (typically 100-1000 nmol) was added.

The contents of the vessel were stirred at 800 rpm. An activator solution (typically 1.1 molar equivalents of dimethyl anilinium tetrakis-pentafluorophenyl borate dissolved in toluene or 100-1000 molar equivalents of methyl alumoxane (MAO) in toluene) was then injected into the reaction vessel along with 500 microliters of toluene, followed by a toluene solution of catalyst (typically 0.40 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a predetermined amount of pressure had been taken up by the reaction. Alternatively, the reaction may be allowed to proceed for a set amount of time. At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight and by DSC (see below) to determine melting point.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580 to 3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1 to 0.9 mg/mL. 250 uL of a polymer solution was injected into the system. The concentration of the polymer in the eluent was monitored using an infrared absorption detector. The molecular weights presented are relative to linear polystyrene standards and are uncorrected.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

TABLE 1

Propylene homopolymerizations. General conditions: 70° C., 120 psi C3, N,N-dimethylanilinum tetrakis(perfluorophenyl)borate (44 nmol), tri-n-octylaluminum (300 nmol) isohexane solvent.

| run | Catalyst complex (40 nmol) | quench t (s) | yield (mg) | activity (kg/mmol/h) | Mw (g/mol) | Mn (g/mol) | Tm (° C.) |
|---|---|---|---|---|---|---|---|
| 1 | 1  | 51 | 193 | 341 | 453,325 | 250,049 | 120.5 |
| 2 | 1  | 59 | 198 | 304 | 472,935 | 246,923 | 121.3 |
| 3 | 2  | 49 | 189 | 345 | 448,126 | 247,234 | 146.7 |
| 4 | 2  | 58 | 204 | 318 | 477,235 | 250,929 | 146.6 |
| 5 | 4* | 54 | 143 | 239 | 682,952 | 359,719 | 143.4 |
| 6 | 4* | 64 | 163 | 229 | 692,247 | 350,672 | 145.1 |

*Comparative examples.

TABLE 2

Propylene homopolymerizations. General conditions: 85° C., 120 psi C3, N,N-dimethylanilinum tetrakis(perfluorophenyl)borate (44 nmol), tri-n-octylaluminum (300 nmol) isohexane solvent.

| run | Catalyst complex (40 nmol) | quench t (s) | yield (mg) | activity (kg/mmol/h) | Mw (g/mol) | Mn (g/mol) | Tm (° C.) |
|---|---|---|---|---|---|---|---|
| 7  | 1  | 63  | 136 | 193 | 283,115 | 158,092 | 119.0 |
| 8  | 1  | 64  | 134 | 187 | 293,016 | 153,699 | 118.7 |
| 9  | 2  | 59  | 124 | 189 | 290,261 | 163,503 | 144.9 |
| 10 | 2  | 65  | 125 | 174 | 301,230 | 163,657 | 144.7 |
| 11 | 3* | 123 | 74  | 54  | 275,789 | 178,580 | 106.2 |
| 12 | 4* | 74  | 101 | 123 | 405,207 | 216,297 | 142.6 |
| 13 | 4* | 70  | 102 | 132 | 425,958 | 224,074 | 142.4 |

*Comparative examples.

For purposes of the claims, the following test methods shall be used.

$^1$H NMR

1H NMR data is collected at 120° C. shall be used in a 5 mm probe using a spectrometer with a 1H frequency of at least 400 MHz. Data is recorded using a maximum pulse width of 45°, 8 seconds between pulses and signal averaging 120 transients. Spectral signals are integrated. Samples are dissolved in deuterated methylene chloride at concentrations between 10 to 15 wt % prior to being inserted into the spectrometer magnet. Prior to data analysis, spectra are referenced by setting the residual CHDCl2 resonance to 5.24 ppm.

$^{13}$C NMR

13C NMR data is collected at 120° C. using a spectrometer with a 13C frequency of at least 75 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra are acquired with time averaging to provide a signal to noise level adequate to measure the signals of interest. Samples are dissolved in deuterated methylene chloride at concentrations between 10 to 15 wt % prior to being inserted into the spectrometer magnet. Prior to data analysis, spectra are referenced by setting the chemical shift of the deuterated methylene chloride solvent signal to 54 ppm.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A pyridyldiamido transition metal complex represented by the formula: (A), (B), (C), or (D):

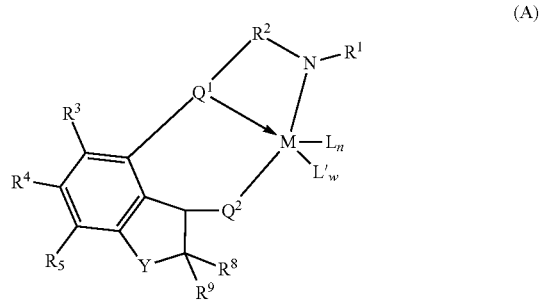

(A)

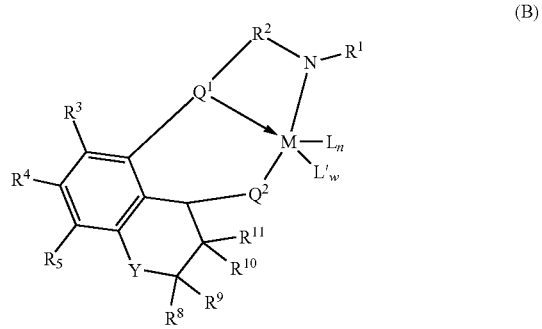

(B)

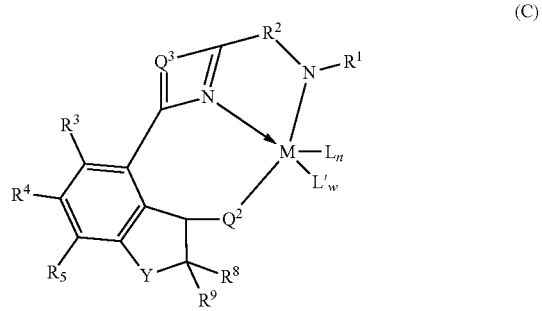

(C)

37
-continued (D)

wherein:

M is a Group 3, 4, 5, 6, 7, 8, 9, 10, 11, or 12 metal;

$Q^1$ is a three atom bridge with the central of the three atoms being a group 15 or 16 element (said group 15 element may or may not be substituted with an $R^{30}$ group) represented by the formula: $-G^1-G^2-G^3-$ where $G^2$ is a group 15 or 16 atom (said group 15 element may be substituted with a $R^{30}$ group), $G^1$ and $G^3$ are each a group 14, 15, or 16 atom (each group 14, 15, and 16 element may or may not be substituted with one or more $R^{30}$ groups), where $G^1$, $G^2$ and $G^3$, or $G^1$ and $G^2$, or $G^1$ and $G^3$, or $G^2$ and $G^3$ may form a singular or multi ring system;

each $R^{30}$ group is, independently, hydrogen or a $C_1$ to $C_{100}$ hydrocarbyl group or a silyl group;

$Q^2$ is $-NR^{17}$, $-PR^{17}$, or oxygen, where $R^{17}$ is selected from hydrogen, hydrocarbyls, substituted hydrocarbyls, silyls, or germyls;

$Q^3$ is -(TT)- or -(TTT)- where each T is carbon or a heteroatom, and said carbon or heteroatom may be unsubstituted or substituted with one or more $R^{30}$ groups that together with the "—C-$Q^3$=C—" fragment, forms a 5- or 6-membered cyclic group or a polycyclic group including the 5 or 6-membered cyclic group;

$R^1$ is selected from the group consisting of hydrocarbyls, substituted hydrocarbyls, and silyl groups;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^2$ is -E($R^{12}$)($R^{13}$)— with E being carbon, silicon, or germanium;

Y is selected from oxygen, sulfur, or -E*($R^6$)($R^7$)—, with E* being carbon, silicon, or germanium;

$R^6$, $R^7$, $R^8$, $R^9$, $R^{10}$, $R^{11}$, $R^{12}$, and $R^{13}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^8$ & $R^9$, and/or R9 & R10, and/or $R^{10}$ & $R^{11}$ and/or $R^{12}$ & $R^{13}$) may be joined to form a saturated, substituted or unsubstituted hydrocarbyl or heterocyclic ring, where the ring has 5, 6, 7, or 8 ring carbon atoms and where substitutions on the ring can join to form additional rings;

38

L is an anionic leaving group, where the L groups may be the same or different and any two L groups may be linked to form a dianionic leaving group;

n is 0, 1, 2, 3, or 4;

L' is a neutral Lewis base; and w is 0, 1, 2, 3, or 4.

2. The complex of claim 1, wherein M is Ti, Zr, or Hf.

3. The complex of claim 1, wherein $R^2$ is selected from $CH_2$, CH(aryl), CH(2-isopropylphenyl), CH(2,6-dimethylphenyl), CH(2,4-6-trimethylphenyl), CH(alkyl), $CMe_2$, $SiMe_2$, $SiEt_2$, or $SiPh_2$.

4. The complex of claim 1, wherein T is C, O, S, or N.

5. The complex of claim 1, wherein E and E* are carbon and each $R^6$, $R^7$, $R^{12}$, and $R^{13}$ are a $C_1$ to $C_{30}$ substituted or unsubstituted hydrocarbyl group.

6. The complex of claim 1, wherein E and E* are carbon and each $R^6$, $R^7$, $R^{12}$, and $R^{13}$ are a $C_6$ to $C_{30}$ substituted or unsubstituted aryl group.

7. The complex of claim 1, wherein $Q^2$ is $-NR^{17}$.

8. The complex of claim 1, wherein E and E* are carbon and $R^1$ and $R^{17}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyl groups with from one to ten carbons.

9. The complex of claim 1, wherein $Q^1$ is selected from:

where the ⌇ symbols indicate the connections to $R^2$ and the aromatic ring, and alkyl is an alkyl group.

10. The complex of claim 1, wherein each L is independently selected from the group consisting of halide, alkyl, aryl, alkoxy, amido, hydrido, phenoxy, hydroxy, silyl, allyl, alkenyl, triflate, alkylsulfonate, arylsulfonate, and alkynyl; and each L' is independently selected from the group consisting of ethers, thio-ethers, amines, nitriles, imines, pyridines, and phosphines.

11. The complex of claim 1, wherein $Q^3$ is CHCHCH, $CH_2CH$, CHN(alkyl), CH—S, CHC(alkyl)=CH, C(alkyl)CH=C(alkyl), CH—O, or NO.

12. The complex of claim 1, wherein the complex is represented by formula (A).

13. The complex of claim 1, wherein the complex is represented by formula (B).

14. The complex of claim 1, wherein the complex is represented by formula (C).

15. The complex of claim 1, wherein the complex is represented by formula (D).

16. A catalyst system comprising an activator and the complex of claim 1.

17. The catalyst system of claim 16, wherein the activator comprises an alumoxane.

18. The catalyst system of claim 16, wherein the activator comprises a non-coordinating anion.

19. The catalyst system of claim 16, wherein the activator comprises one or more of:
trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, N,N-dimethylanilinium tetrakis(3,5-bis(trifluoromethyl)phenyl)borate, triphenylcarbenium tetrakis(3,5-bis(trifluoromethyl)phenyl)borate, triphenylcarbenium tetrakis(perfluorophenyl)borate [$Ph_3C^+$][$B(C_6F_5)_4^-$], [$Me_3NH^+$][$B(C_6F_5)_4^-$], 1-(4-(tris(pentafluorophenyl)borate)-2,3,5,6-tetrafluorophenyl)pyrrolidinium, triphenylcarbenium tetraphenylborate, and triphenylcarbenium tetrakis-(2,3,4,6-tetrafluorophenyl)borate.

20. A polymerization process comprising contacting one or more alkene monomers with a catalyst system comprising: i) an activator and ii) the pyridyldiamido transition metal complex of claim 1.

21. The process of claim 20, wherein the activator comprises an alumoxane.

22. The process of claim 20, wherein the activator comprises a non-coordinating anion.

23. The process of claim 20 wherein the monomer comprises ethylene.

24. The process of claim 20 wherein the monomer comprises propylene.

25. The process of claim 20 wherein the pyridyldiamido transition metal complex is supported.

26. The process of claim 25 wherein the support is silica.

27. The process of claim 20, wherein the activator comprises one or more of:
trimethylammonium tetrakis(perfluoronaphthyl)borate, N,N-dimethylanilinium tetrakis(perfluoronaphthyl)borate, N,N-diethylanilinium tetrakis(perfluoronaphthyl)borate, triphenylcarbenium tetrakis(perfluoronaphthyl)borate, trimethylammonium tetrakis(perfluorobiphenyl)borate, N,N-dimethylanilinium tetrakis(perfluorobiphenyl)borate, triphenylcarbenium tetrakis(perfluorobiphenyl)borate, N,N-dimethylanilinium tetrakis(3,5-bis(trifluoromethyl)phenyl)borate, triphenylcarbenium tetrakis(3,5-bis(trifluoromethyl)phenyl)borate, triphenylcarbenium tetrakis(perfluorophenyl)borate [$Ph_3C^+$][$B(C_6F_5)_4^-$], [$Me_3NH^+$][$B(C_6F_5)_4^-$], 1-(4-(tris(pentafluorophenyl)borate)-2,3,5,6-tetrafluorophenyl)pyrrolidinium, triphenylcarbenium tetraphenylborate, and triphenylcarbenium tetrakis-(2,3,4,6-tetrafluorophenyl)borate.

\* \* \* \* \*